(12) United States Patent
Schultz-Fademrecht et al.

(10) Patent No.: US 8,226,982 B2
(45) Date of Patent: Jul. 24, 2012

(54) INHALABLE POWDERS COMPRISING PROTEIN, PHENYLALANINE, AND OTHER PROTEIN STABILIZERS

(75) Inventors: Torsten Schultz-Fademrecht, Maselheim (DE); Patrick Garidel, Norderstedt (DE); Beate Fischer, Bad Waldsee (DE); Karoline Bechtold-Peters, Biberach (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 1163 days.

(21) Appl. No.: 11/766,940

(22) Filed: Jun. 22, 2007

(65) Prior Publication Data
US 2008/0089849 A1    Apr. 17, 2008

Related U.S. Application Data

(60) Provisional application No. 60/806,685, filed on Jul. 6, 2006.

(30) Foreign Application Priority Data

Jun. 29, 2006   (DE) .......................... 10 2006 030 164

(51) Int. Cl.
| | |
|---|---|
| A61K 9/00 | (2006.01) |
| A61K 9/14 | (2006.01) |
| A61K 31/195 | (2006.01) |
| A61K 38/00 | (2006.01) |
| A61K 38/18 | (2006.01) |
| A61K 38/23 | (2006.01) |
| A61K 38/28 | (2006.01) |

(52) U.S. Cl. ............ 424/489; 424/46; 514/1.1; 514/5.9; 514/7.6; 514/11.9; 514/561

(58) Field of Classification Search .................... 424/46, 424/489; 514/1.1, 5.9, 7.6, 11.9, 561
See application file for complete search history.

(56) References Cited

U.S. PATENT DOCUMENTS
| | | |
|---|---|---|
| 6,372,258 B1 | 4/2002 | Platz et al. |
| 6,956,021 B1 | 10/2005 | Edwards et al. |
| 2007/0298116 A1 | 12/2007 | Bechtold-Peters et al. |

FOREIGN PATENT DOCUMENTS
| | | |
|---|---|---|
| JP | 55102519 A | 8/1980 |
| JP | 61118325 A | 6/1986 |
| WO | WO 95/31479 A1 | 11/1995 |
| WO | WO 96/32096 A1 | 10/1996 |
| WO | WO 97/03649 A1 | 2/1997 |
| WO | WO 02/11695 A2 | 2/2002 |

OTHER PUBLICATIONS

Akagi et al. "Preparation and characterization of biodegradable nanoparticles based on poly(gamma-glutamic acid) with L-phenylalanine," Journal of Controlled Release, 2005, 108, pp. 226-23.*
"Cystic Fibrosis," Medline Plus Medical Encyclopedia, accessed online on Jul. 11, 2008 at www.nlm.nih.gov/medlineplus/ency/article/000107.htm.*
"Lung Cancer," Merck Manual Home Edition accessed online at www.merckmanuals.com/home/lung_and_airway_disorders/cancer_of_the_lungs/lung_cancer.html#v728099 on Feb. 25, 2012.*
Chronic Obstructive Pulmonary Disease, accessed at www.merck.com/mmhe/print/sec04/ch045/ch04a.html at the online Merck Manual Home edition on Mar. 21, 2010.*
"Alpha1-Antitrypsin Deficiency," Merck Manual Home edition accessed online at www.merck.com/mmhe/print/sec04/ch045/ch045b.html on Apr. 23, 2011.*
"Human Immunodeficiency Virus," Merck Manual Home Edition, accessed online on Feb. 25, 2012 at www.merckmanuals.com/home/infections/human_immunodeficiency_virus_hiv_infection/human_immunodeficiency_virus_infection.html#v789182.*
"Asthma," Merck Manual Home Edition, accessed at www.merck.com/mmhe/print/sec04/ch044/ch044a.html on May 5, 2010.*
"Inflammation," Wikipedia article accessed at en.wikipedia.org/wiki/Inflammation on Feb. 25, 2012.*
Abstract in English for JP61118325, Jun. 5, 1985, Yamanouchi Pharma Co. Ltd.
Abstract in English for JP55102519, May 8, 1980, Green Cross Corp.

* cited by examiner

Primary Examiner — James H. Alstrum-Acevedo
(74) Attorney, Agent, or Firm — Michael P. Morris; Anthony P. Bottino

(57) ABSTRACT

The invention therefore relates to protein-containing powders, wherein the proportion of phenylalanine is at least 30% (w/w), or at least 40% (w/w). It has been shown that phenylalanine-containing powders, particularly after spray drying, are very suitable in terms of their aerodynamic characteristics and protein stabilization for preparing powders or protein compositions with improved aerodynamic properties. The main component is phenylalanine and the optional further component is an excipient which has good water-solubility compared with phenylalanine, preferably a sugar or a polyol.

39 Claims, 16 Drawing Sheets

INHALABLE POWDERS COMPRISING PROTEIN, PHENYLALANINE, AND OTHER PROTEIN STABILIZERS

This application claims priority benefit from German application DE 10 2006 030 164.1, filed Jun. 29, 2006, and from U.S. provisional application Ser. No. 60/806,685, filed Jul. 6, 2006, the contents of which are incorporated herein by reference in their entireties.

BACKGROUND TO THE INVENTION

1. Technical Field

The invention relates to phenylalanine-containing powders, particularly spray-dried powders, which contain at least phenylalanine and a protein, the protein preferably being an active substance and particularly a pharmaceutical active substance. The inventive powders contain a phenylalanine fraction of at least 30% (w/w), preferably 40% (w/w) and optionally at least one second pharmaceutically acceptable excipient, namely a sugar, which enhances the protein stability. The invention further relates to a process for preparing these phenylalanine-containing powders as well as the use thereof particularly as inhalative pharmaceutical compositions. Preferred proteins are pharmaceutical active substances such as antibodies, parts of antibodies, fusion proteins with antibodies or parts of antibodies, hormones, growth factors, enzymes, cytokines, interferons or the like for local treatment of the airways or for systemic treatment.

2. Background

Protein preparations or active substances/active substance preparations formulated in aqueous solutions are in some cases prone to instability which may lead to reduced efficacy or bioactivity and increased toxicity or incompatibilities. This applies both to conventional pharmaceuticals and to proteins and particularly active substances containing peptides or proteins. The stability of proteins or pharmaceutical active substances may be favourably influenced by altering the structure (internal) or by adding suitable excipients (external).

A conventional method of externally stabilising proteins or pharmaceutical active substances is the use of suitable excipients. Excipients may be divided roughly into the following categories: sugars and polyols, amino acids, amines, salts, polymers and surfactants.

Sugars and polyols are frequently used as non-specific stabilisers. Their stabilising effect in proteins or biological active substances is predominantly put down to "preferential exclusion" (Xie and Timasheff, 1997, Biophysical Chemistry, 64(1-3), 25-43; Xie and Timasheff, 1997, Protein Science, 6(1), 211-221; Timasheff, 1998, Advances in protein chemistry, 51, 355-432). When choosing sugars, reducing sugars are usually avoided in the case of proteins or biological active substances. Saccharose and trehalose, being non-reducing sugars, are preferably used. Further examples of suitable excipients are glucose, sorbitol, glycerol (Boctor and Mehta, 1992, Journal of Pharmacy and Pharmacology, 44 (7), 600-3; Timasheff, 1993, Annual review of biophysics and biomolecular structure, 22, 67-97; Chang et al., 1993, Pharmaceutical Research, 10(10), 1478-83) and mannitol (Hermann et al., 1996, Pharmaceutical Biotechnology, 9 (Formulation, Characterization, and Stability of protein Drugs) 303-328; Chan et al., 1996, Pharmaceutical Research, 13(5), 756-761). It is also known that all kinds of polymers have a stabilising effect on proteins or pharmaceutical active substances such as for example antibodies. Human serum albumin (HAS) which has frequently been used in the past does indeed have very good stabilising properties but because of its potential contamination with "blood-borne" pathogens it is unsuitable in the mean time. Of the polymers known hitherto, hydroxypropyl-β-cyclodextrin (HP-β-CD) has proved particularly suitable, as it can also be safely administered parenterally. Other examples are higher-molecular dextrans (18 to 82 kD), polyvinylpyrrolidones (PVP), heparin, type A and B gelatine as well as hydroxyethyl-starch (HES), heparin, dextran sulphate, polyphosphoric acid, poly-L-glutamic acid, poly-L-lysine.

In addition to sugars and polyols, amino acids may also be used as stabilisers, on their own or in conjunction with other excipients. Preferably amino acids are used in the stabilisation of proteins. For example the addition of histidine, glycine, sodium-aspartate (Na-Asp), glutamate and lysine hydrochloride (Lys-HCl) inhibits the aggregation of rhKGF in 10 mM sodium phosphate buffer (pH 7.0) together with 5% mannitol (Zhang et al., 1995, Biochemistry, 34 (27), 8631-41). The combination of amino acids and propyleneglycol improves for example the structural stability of rhCNTF (Dix et al, 1995, Pharmaceutical Research (Supplement), 12, S97). Lysine and arginine increase the heat stability of IL-1R (Tm increase), whereas glycine and alanine have a destabilising effect (Remmele et al., 1998, Pharmaceutical Research, 15(2), 200-208).

Moreover, the stability of powders containing protein or pharmaceutical active substances can be increased by various drying processes. The drying is usually carried out in the presence of excipients which should maintain the stability of the proteins or active substances and improve the properties of the dry powders. A crucial factor in stabilising by drying is the immobilisation of the protein or active substance in an amorphous matrix. The amorphous state has high viscosity with low molecular mobility and low reactivity. Advantageous excipients must therefore be capable of forming an amorphous matrix with the highest possible glass transition temperature in which the protein or active substance is embedded. The choice of excipients thus depends particularly on their stabilising qualities. In addition, however, factors such as the pharmaceutical acceptance of the excipient and its influence on particle formation, dispersibility and flow properties play a decisive role, particularly in spray-drying processes.

Spray-drying is a particularly suitable process for increasing the chemical and physical stability of proteins or pharmaceutical active substances of the peptide/protein type (cf. Maa et al., 1998, Pharmaceutical Research, 15(5), 768-775). Particularly in the field of pulmonary treatment spray drying is increasingly used (U.S. Pat. No. 5,626,874; U.S. Pat. No. 5,972,388; Broadhead et al., 1994, J. Pharm Pharmacol., 46(6), 458-467), as administration by inhalation is now an alternative in the treatment of systemic diseases (WO 99/07340). The prerequisite for this is that the mean aerodynamic particle size (MMAD=mass median aerodynamic diameter) of the powder particles is in the range from 1-10 μm, preferably 1-7.5 μm, so that the particles can penetrate deep into the lungs and thus enter the bloodstream. DE-A-179 22 07, for example, describes the preparation of corresponding spray dried particles. In the meantime a number of methods of producing corresponding powders have been described (WO 95/31479; WO 96/09814; WO 96/32096; WO 96/32149; WO 97/41833; WO 97/44013; WO 98/16205; WO 98/31346; WO 99/66903; WO 00/10541; WO 01/13893; Maa et al., 1998, supra; Vidgrén et al., 1987, Int. J. Pharmaceutics, 35, 139-144; Niven et al., 1994, Pharmaceutical Research, 11(8), 1101-1109).

Sugar and alcohols thereof such as, for example, trehalose, lactose, saccharose or mannitol and various polymers have proved suitable as excipients (Maa et al., 1997, Pharm. Development and Technology, 2(3), 213-223; Maa et al., 1998, supra; Dissertation Adler, 1998, University of Erlangen; Costantino, et al., 1998, J. Pharm. Sci., 87(11), 1406-1411).

However, the excipients predominantly used have various drawbacks. The addition of trehalose and mannitol, for example, impairs the flow properties of spray-drying formulations (C. Bosquillon et al., 2001 Journal of Controlled Release, 70(3), 329-339). Spray-dried trehalose often causes serious sticking of the resulting particles (L. Mao et. al, 2004 Respiratory Drug Delivery IX, S. 653-656). This is associated with technical processing problems connected with the yields of powder and the robustness of the process, as well as a deterioration in the bioavailability of the powder for pulmonary application, caused by a reduction in the fine particle fraction that can be obtained. Moreover, mannitol has a tendency to recrystallise in amounts of more than 20 percent by weight (Costantino et al., 1998, supra), as a result of which its stabilising effects are dramatically reduced. Lactose, a frequently used excipient, does improve the flow properties of spray-drying formulations (C. Bosquillon et al., 2001, supra), but is problematic particularly in the formulation of proteins or peptide/protein-containing active substances, as lactose can enter into destabilising Maillard reactions with peptides/proteins as a result of its reducing property.

Besides protein stabilisation using excipients, however, optimising the physicochemical properties of spray-dried powders is the focus of the recipe development. In particular, powders, particularly spray-dried powders, have a tendency to cohesive and adhesive characteristics. One important reason for this is the particles size of <10 μm which is necessary for pulmonary administration. At these small particle sizes, particle interactions such as e.g. Van-der-Waals forces, capillary forces, dipolar interactions and electrostatic interactions, predominate over gravitational forces. [I. Zimmermann, Pharmazeutische Industrie, Springer-Verlag]. Whereas capillary forces caused by water vapour condensation can be controlled by suitable storage of the powders at reduced humidity, the Van-der-Waals forces and the electrostatic interactions between the (spray-dried) particles have proved a major challenge.

The interparticle interactions can be reduced by making the particle surface hydrophobic. This can be done by dissolving hydrophobic substances as additives with the protein or active substance and other suitable excipients and spray-drying them. The state of the art for rendering surfaces hydrophobic consists, inter alia, of the hydrophobic amino acid L-leucine (L. Mao et. al, 2004 Respiratory Drug Delivery IX, S. 653-656, A R. Najafabadi et al., 2004, Int J. Pharm. 2004 Nov. 5; 285(1-2):97-108). As only the surface coating is to be modified in this process, the amount of L-leucine needed is only 5-10 percent by weight (% w/w). Increasing the proportion of amino acid often leads to undesirable crystallisation effects, damaging the protein (Dissertation by Richard Fuhrherr, 2005, LMU Uni, Munich). The addition of other amino acids such as e.g. DL-asparagine, DL-arginine, DL-methionine, DL-phenylalanine and DL-tryptophan (N. Y. K. Chew et. al, 2002 Respiratory Drug Delivery VIII, S. 743-745) to the protein and preferably to the spray solution may have a beneficial effect on the aerodynamic characteristics of the particles. Besides the direct addition of the hydrophobic substance to the protein and particularly to the spray solution, the powder particles may be coated with additives in a further step. Substances which are particularly suitable for this are L-leucine, phospholipids and Mg-stearate (WO2004093848). Potential coating methods use gravity mixers, e.g. tumble mixers (US2005152849), but also mechanical mixing methods such as e.g. jet grinding (WO2004093848).

A conventional method of administering proteins and peptides is by parenteral administration. The active substance may for example be given intravenously, intramuscularly and subcutaneously. The state of the art is to administer the medicament through a cannula, e.g. combined with a syringe, a pen or as an infusion using an infusion bag. A disadvantage of this is that powder formulations have to be reconstituted in liquid before they are administered. Moreover, parenteral administration is not popular with patients because of needle phobia, a common complaint. For these reasons, parenteral treatments often have to be given by the doctor. By contrast, systemic inhaled formulations can be administered by the patients themselves.

Proteins/peptides can enter the bloodstream by passive diffusion or by active transportation through the lungs. In passive transportation, the absorption rate is a function of the size of the molecule of the active substance [J. S. Patton, Nature Biotechnology, 16, 141ff, 1998].

Whereas with small proteins such as insulin, for example, good bioavailablilities have been found (J. S. Patton, 1999 Advanced Drug Delivery Review, 35, 235-247) larger proteins and especially antibodies generally have a very low absorption rate. In order to develop an efficient form of medication, in spite of this, larger proteins have to be transported actively through the lung epithelium by specific mechanisms.

One possibility for actively transporting antibodies through the lung epithelium is the neonatal Fc-receptor (A. Bitonti, 2004, Respiratory Drug Delivery IX 0.79-85). It has been found that these receptors are present in sufficiently large numbers in the lungs not only of neonates but also in children and adults and can be used for actively transporting active substances.

When preparing powders containing protein for medical applications, particularly spray-dried powders or protein compositions, a particular challenge is to achieve, in addition to good protein stability, the most advantageous aerodynamic characteristics possible, so that the powders or the particles thereof, particularly spray-dried powders and particles, can penetrate deep into the lungs and thus easily enter the bloodstream.

In recent times more and more inhalable drugs have been developed (inhalable insulin as a development product made by Messrs Aradigm, Mannkind or Kos, K. Corkery, Respiratory Care, 45, 831ff, 2000) or are already on the market (e.g. Pulmozyme® as an inhaled form of recombinant human deoxyribonuclease I (rhDNase) or Exubera as an inhaled form of human insulin, cf. U.S. Pat. No. 5,997,848), for treating a variety of diseases. It has been found that certain drugs are easily absorbed in the lungs through the alveoli directly into the bloodstream. Administration by inhalation is particularly promising for administering macromolecules such as proteins, polypeptides and nucleic acids, which are difficult to administer by other routes (e.g. orally). This administration by inhalation may be effectively used both for systemic diseases and for local diseases of the lungs.

Pulmonary drug administration can be carried out by various methods, e.g. using liquid nebulizers, propellant-based inhalers (aerosol-based metered-dose inhalers=MDI), and dry powder dispersion devices. The development of propellant-based formulations is associated with a range of problems. Thus, the established chlorofluorocarbons (CFC's) can no longer be used, on account of their ozone-damaging properties. As a substitute alternative propellant gases may be used (HFA-143a/HFA227). The alternative propellant gases however often exhibit reduced solubility of the active substance, compared to the CFC's. In addition, the stability of the suspension is critical when preparing suspensions, with the result that further excipients are needed as mediators between the propellant gas and the particle. High dosage settings, such as are often needed antibodies, are difficult to achieve using MDI's. These factors have meant that MDI's have become more and more preferable for peptide and protein recipes. Dry powder dispersion devices, which are not dependent on propellant gas aerosol technology, are promising in the application of medicaments, which can easily be formulated as dry powders.

Many otherwise unstable macromolecules may be stabilised in the form of powders, particularly lyophilised or spray-dried powders, on their own or in conjunction with suitable excipients. However, the ability to administer pharmaceutical compositions as dry powders has its own problems. The metering of many pharmaceutical compositions is often critical. For this reason it is essential that every system for administering dry powder also administers the intended dose accurately, precisely and reliably in reality. This is not reliably ensured with the systems known hitherto. In addition, many drugs are very expensive. It is therefore important that the dry powder should be able to be delivered efficiently. It is also important that the powder is easily dispersible (capable of flight) before it is inhaled by the patient, so ensure adequate distribution and system absorption. These points are not ideally satisfied in the majority of conventional powders containing a protein or pharmaceutical active substance.

The problem therefore arises that in the powders used hitherto which contain a amount of protein, particularly spray-dried powders or protein compositions with pharmaceutical active substance, efficient and optimum pulmonary administration is not possible. Admittedly, it has been possible to achieve good protein stability in the powders used hitherto, but not optimum aerodynamic properties. For example large amounts of antibody in the powder, particularly in the spray-dried powder, causes severe clumping of the primary particles. These clumps are difficult to disperse, and this negatively affects the aerodynamic properties (doctoral thesis of Stefanie Schüle, Uni LMU 2005).

Thus the protein or pharmaceutical active substance which is to be administered has to be dosed in significantly larger amounts than are actually required, as, of the active substance used, only a fraction reaches the target site in the lungs. The danger of the side effects is also greater than when dosing is efficient.

The problem thus arises of providing alternative powders, particularly spray-dried powders or protein compositions, which in addition to having sufficient protein stability also have very good or improved aerodynamic properties.

A further aim of the invention is to provide corresponding alternative powders, particularly spray-dried powders or protein compositions, for use by inhalation, particularly for pharmaceutical or medical applications.

The problems on which the invention is based are solved by the following embodiments and by the objects and methods recited in the claims.

SUMMARY OF THE INVENTION

The present invention relates to powders, particularly spray-dried powders, containing a protein and phenylalanine as well as optional a sugar, characterised in that the powder contains at least 30% (w/w) phenylalanine, preferably at least 40% (w/w) phenylalanine.

The present invention further relates to a pharmaceutical composition, particularly a spray-dried composition, containing a protein and phenylalanine as well as optionally a further excipient such as a sugar or a polyol, characterised in that the powder contains at least 30% (w/w) phenylalanine, preferably at least 40% (w/w) phenylalanine.

The present invention further relates to a process for preparing a powder characterised in that
a) a phenylalanine solution is prepared,
b) at least one protein and optionally at least one further excipient such as a sugar or a polyol are added,
c) the solution or suspension thus obtained at an inflow temperature of preferably 90-200° C. and an outflow temperature of preferably 40-150° C. is sprayed and
d) the particles formed are separated from the drying gas.

The present invention also relates to the use of the above-mentioned powder as a medicament and particularly as an inhaled medicament and the use of the above-mentioned powder for preparing a medicament for the treatment of respiratory complaints or systemic diseases such as lung cancer, inflammation of the lung, cystic fibrosis, COPD (chronic obstructive pulmonary disease), asthma, anti-inflammatory diseases, diseases caused e.g. by the respiratory-syncytial virus (RSV).

It has been shown that binary and ternary powders containing a protein are very well suited, in terms of their aerodynamic characteristics and protein stabilisation after spray-drying, to the preparation of alternative, preferably spray-dried powders or protein compositions with exceptional aerodynamic properties. The main component is phenylalanine and the optional further component is an excipient with good water-solubility compared with phenylalanine, such as a sugar or a polyol.

The high proportion of phenylalanine is critical for the manufacture of the powder. As a result of its low solubility and high hydrophobicity the phenylalanine accumulates on the surface of the particles and is therefore responsible for the surface structure and particle morphology. Readily water-soluble components, such as e.g. the sugars lactosucrose (LS90P) or saccharose and the protein should therefore be precipitated mainly inside the core and form an amorphous matrix.

It has also been shown that other amino acids with similar properties in terms of hydrophobicity and solubility (e.g. valine, leucine or isoleucine) do not yield correspondingly good aerodynamic characteristics of the powders and are accordingly unsuitable for the preparation of powder formulations containing at least 30% (w/w) phenylalanine, preferably at least 40% (w/w) phenylalanine or the other phenylalanine % (w/w) contents mentioned.

It has also been shown that the particle morphology is highly dependent on the phenylalanine content in the spray-dried powder. At phenylalanine contents of 50% (w/w), 40% (w/w) and 30% (w/w), highly creased, raisin-like particles are obtained (FIG. 10a-10c). When the phenylalanine content is reduced to 20% the intensity of creasing decreases sharply. The change in the particle morphology correlates with the deterioration in the aerodynamic characteristics of the powder. This means that the positive effect of the phenylalanine when spray-drying spray solutions only becomes apparent upwards of 30% (w/w).

Tests with other aromatic amino acids yielded the following results. Tyrosine has too low a water-solubility to be considered as a formulation component.

With tryptophan only a powder formulation with a 20% tryptophan content could be prepared. With these small amounts, no technical advantage of the tryptophan could be detected in the spray-drying and particularly in the aerodynamic characteristics.

Histidine-containing powder is highly sensitive to humidity in the air, compared with the phenylalanine-containing powder. Therefore, a major advantage of the phenylalanine-containing powder over the histidine-containing powder is its lower moisture-sensitivity. Whereas the FPF of the histidine-containing powder breaks down after exposure to 50% relative humidity, in the case of the phenylalanine-containing powder the FPF is even improved after exposure to moisture. Corresponding characteristics can also be observed in relation to the expelled mass. In the case of the histidine-containing powder the expelled mass decreases on exposure to moisture, whereas in the case of the phenylalanine-containing powder it increases.

To summarise, it may be said that the positive properties of phenylalanine on spray-drying cannot be achieved using other aromatic amino acids.

Furthermore crystallisation inhibitors such as HSA may improve the particle properties of powders. Crystallisation inhibitors assist the formation of an amorphous matrix within the core of the particle where the readily water-soluble components such as the sugars and the protein are located.

It has also been shown that by a skilful choice of excipients the positive effect of phenylalanine on the spray drying process can be further improved. The further excipient is not restricted to one category of substances. It may be, as in this example, a sugar or sugar alcohol, an amino acid or a polymer. What is crucial to the use of the further excipient is the stabilisation of the protein during spray drying. It is also apparent that by adding another excipient the protein can be stabilised, compared with binary mixtures of phenylalanine and IgG1.

The invention does not arise from the prior art.

For improving the particle properties of pharmaceutical powders for pulmonary administration particularly by spray drying methods are known in the art, such as e.g. the possibility of rendering the particle surfaces hydrophobic in U.S. Pat. No. 6,372,258 and US2005/0152849. U.S. Pat. No. 6,372,258 uses hydrophobic amino acids, including phenylalanine, for preparing spray-dried powders.

In this process hydrophobic amino acids are added to the spray solution besides the protein or active substance and sprayed in dissolved form and dried. As a result of the hydrophobic properties of the amino acid enrichment of the amino acid in the atomised drop takes place on the surface of the drop, resulting eventually in an enrichment on the particle surface. The hydrophobic coating reduces the affinity of the water for the powder. This is connected with a reduction in the capillary forces caused by a lower water-vapour condensation and a reduction in the dipolar interactions.

U.S. Pat. No. 6,372,258 however describes neither the particularly advantageous aerodynamic effect of phenylalanine in minimum amounts of 30% (w/w), or 40% (w/w) compared with other hydrophobic amino acids such as leucine or tryptophan nor the particularly advantageous effects of ternary complexes of 30% (w/w), preferably 40% (w/w) phenylalanine, a further excipient, preferably a sugar or polyol, and a protein, particularly a protein active substance.

In WO970364 or US2005/0152849 the crux is the mixing of the active substance with a so-called anti-adherent agent.

The applications describe inter alia the use of leucine as an anti-adherent material which is used to coat the particles so as to prevent them from clumping together. According to US2005/0152849 however not more than 10% of the powder should consist of the excipient.

EP 0913177 describes a process for preparing dry, amorphous products containing biologically active materials by convection drying, particularly spray drying. In the disclosed mixtures of protein (EPO), sugar and amino acids (in some cases with Tween 20 as well), however, the proportion of sugar is always greater than the proportion of the amino acids. In addition, 2 amino acids are always used. Furthermore in contrast to the experiments in EP 0913177 in the present invention the amino acid is not titrated to its isoelectric point. The particularly advantageous aerodynamic characteristics (FPF, expelled mass) of the present powders according to the invention is not restricted to the isoelectric point of phenylalanine. The powders prepared at different pH values were partly crystalline in each case. Accordingly, the pH of the spray solution is not crucial to the properties of the powders (dispersibility/inhalability) and the spray qualities of the phenylalanine. The protein stabilisation does indeed depend on the pH of the spray solution (the antibody used is more stable at low pH values), but protein stabilisation can also be achieved at high pH values of 9.0, particularly compared with binary compositions.

In WO0033811, in particular, amino acid-containing particles are prepared having a low density (not more than 0.1 g/cm$^3$). One possible method is spray drying.

However, on the one hand the amino acid content does not exceed the 20% mark and on the other hand the crux of the disclosure of WO0033811 is leucine. Phenylalanine is not mentioned in WO0033811.

In JP62281847 spray drying has been carried out with pure phenylalanine. However, the focus was not on the Inhalation. The particle sizes obtained are therefore substantially greater.

The prior art also teaches the spraying of the amino acids asparagine, arginine, leucine, methionine, phenylalanine and tryptophan with a protein (N. Y. K. Chew et. al, 2002 Respiratory Drug Delivery VIII, S. 743-745). The amino acid content was generally 5% (w/w). The exception was leucine; here an additional 10% (w/w) amino acid content was sprayed. Depending on the flow rate and equipment, an improvement in the FPF was found in all the amino acids. The best effect however was obtained with leucine. Using a Dinkihaler and a flow rate of 120 L/min, FPFs of between 55-60% (w/w) could be measured with phenylalanine as well. A restriction over the service invention is to be found in the proportion of phenylalanine. Moreover, no ternary mixtures were used in the study by Chew at al.

DESCRIPTION OF THE FIGURES

All the percentages stated in the descriptions are based on concentration data and compositions of the dry solids, particularly in a powder obtained by spray drying (W/W).

SEM Photographs of Spray-Dried Powder Containing an IgG1 Antibody and an Amino Acid:

The photographs were taken with a scanning electron microscope (SUPRA 55 VP, Messrs. Zeiss SMT, Oberkochen). For this, the powder samples were sprinkled directly onto suitable sample plates. Excess material was knocked off and blow away. Then the samples were coated with 10 nm of gold/palladium to ensure adequate electrical conductivity.

Figure 2:
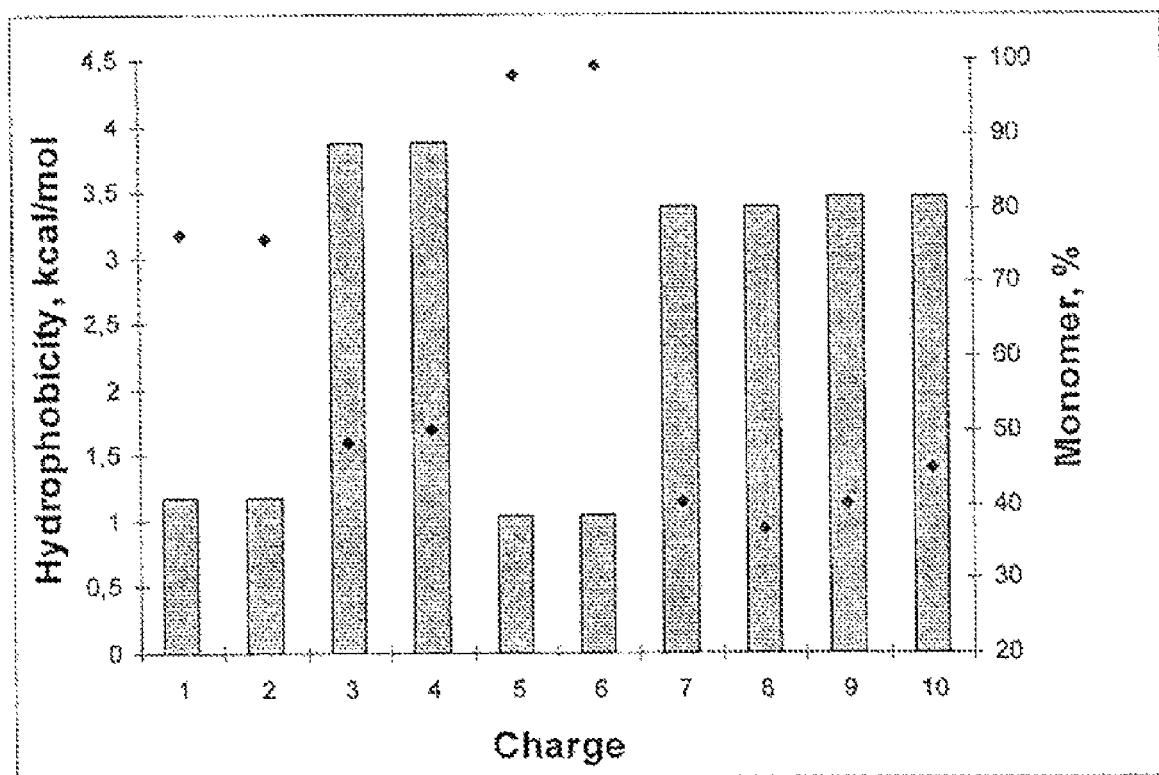
Figure 3A:
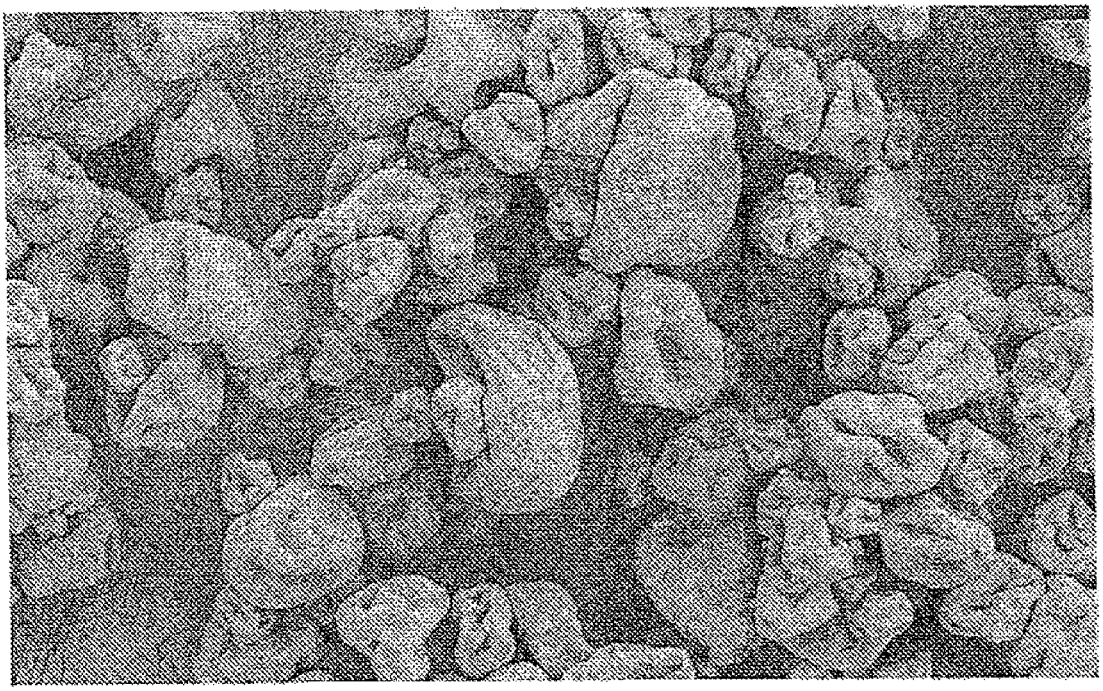
Figure 3B:
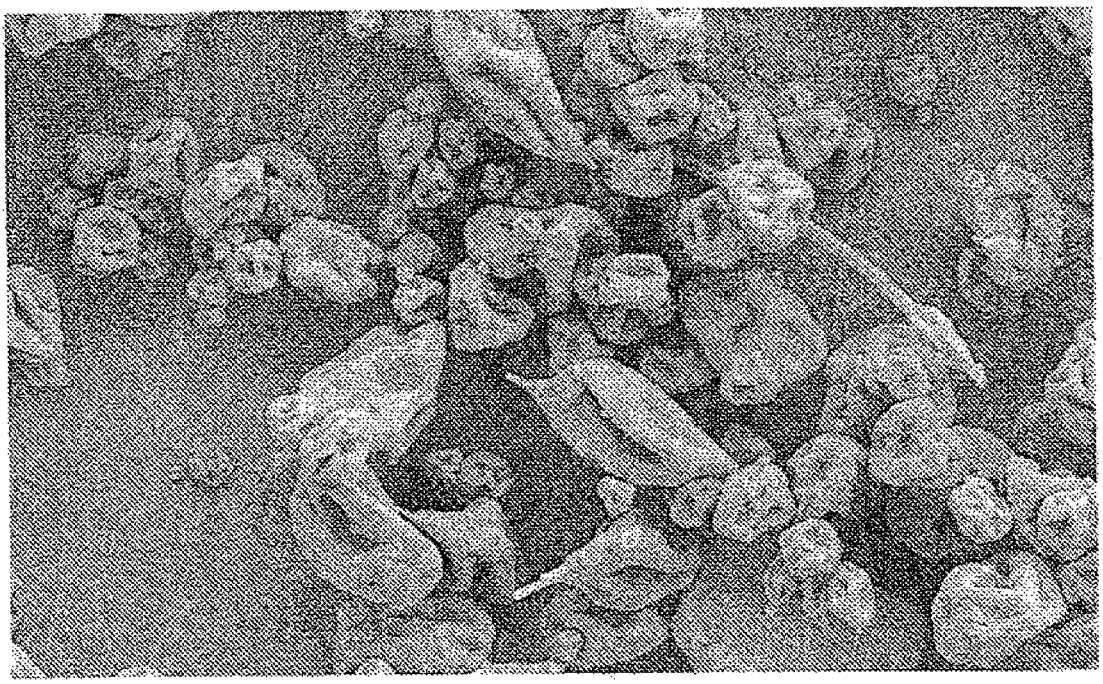
Figure 3C:
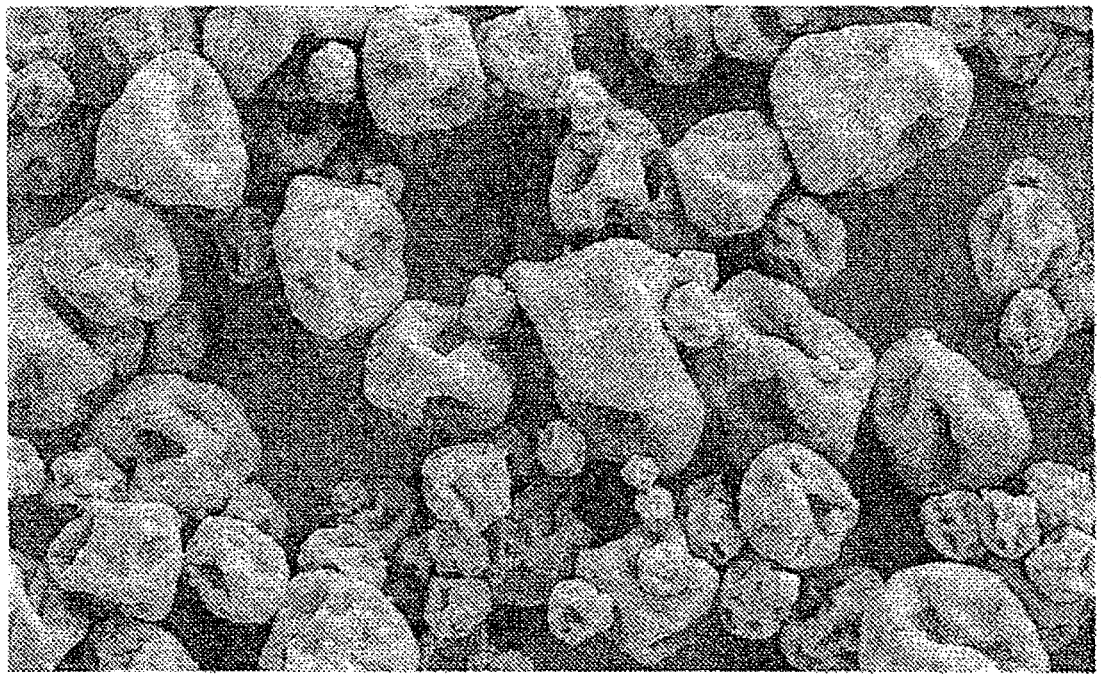
Figure 3D:
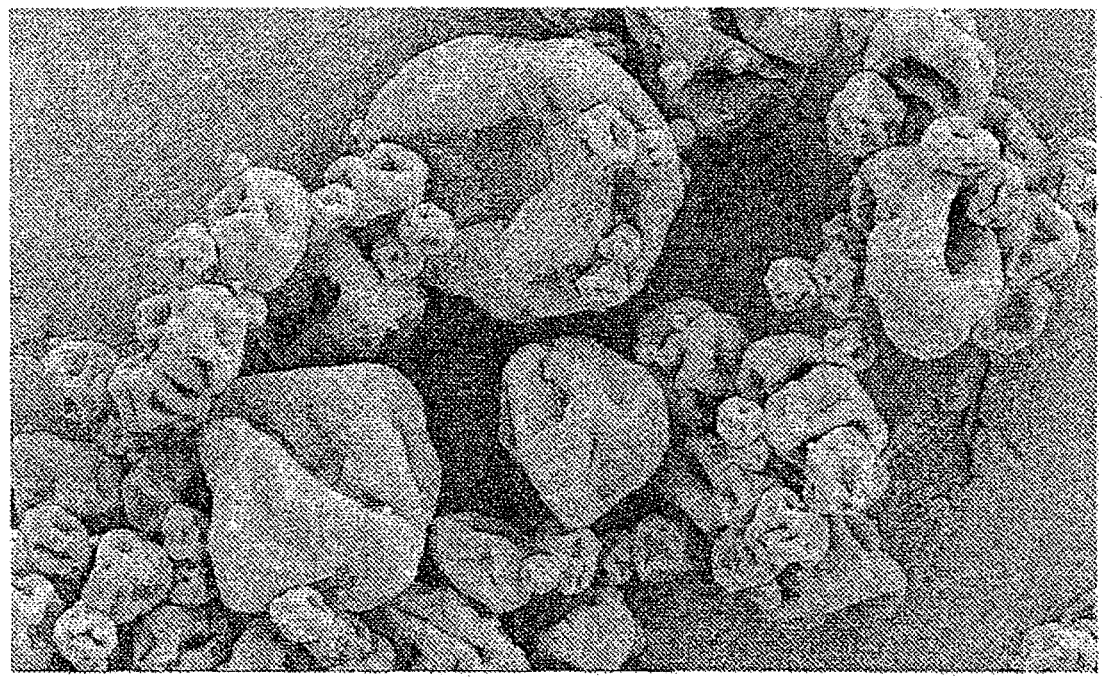

Detection for displaying the images was carried out using secondary electrons.

a) Composition of the Spray-Dried Powder: 90% Valine/10% IgG1
magnification: 5000×
distance from powder to cathode: 8 mm
shutter size: 20 µm
acceleration voltage: 6 kV
vacuum: 5.73e-005 Pa b) Composition Spray-Dried Powder: 90% Isoleucine/10% IgG1
magnification: 3000×
distance from powder to cathode: 8 mm
acceleration voltage: 6 kV
vacuum: 5.47e-005 Pa c) Composition Spray-Dried Powder: 90% Phenylalanine/10% IgG1
magnification: 5000×
distance from powder to cathode: 8 mm
acceleration voltage: 6 kV
vacuum: 5.73e-005 Pa FIG. 2:
Comparison of the Hydrophobicity of Various Amino Acids and the Protein Monomer Contents after Spray Drying Binary Mixtures as a Function of the Solids Concentration in the Spray Solution (50% and 90% Achieved Solubility Limit of the Amino Acid):

In this Figure the protein stabilisation after spray drying is compared with the hydrophobic fractions of the amino acids used. There are a number of ways of stating the hydrophobicity of amino acids (P. Andrew Karplus, Hydrophobicity regained, Protein science (1997), 6: 1302-1307). One common method is to specify the free enthalpy when transferring a substance from a solvent into water (e.g. $\Delta G°_{trans\ oct/water}$). The disadvantage of this method is the fact that the results are strongly dependent on the measuring conditions (e.g. choice of solvent). Particularly with polar substances there may be such large differences in the results. Pure observation of the hydrophobic surfaces, on the other hand, is independent of the measuring conditions. Therefore, in this Figure, only the hydrophobic portions or areas of the amino acid groups are taken into consideration. Aliphatic $CH_2$ groups are assigned an enthalpy of 25 cal/Å$^2$ and aromatic CH groups an enthalpy of 16 cal/Å$^2$. This observation does not take account of any polar fractions or inductive effects produced by the electronegativity.

The tendency to form protein aggregates was determined by exclusion chromatography (HP-SEC). Exclusion was carried out using the molecular size of the protein or its aggregates (e.g. dimers). It is known that aggregate formation is associated with protein destabilisation.

Compositions of the Spray-Dried Powders:

| Charge 1: | 10% IgG1/90% isoleucine, solid fraction: 3.5% |
| Charge 2 | 10% IgG1/90% glycine, solid fraction: 20.2% |
| Charge 3 | 10% IgG1/90% valine, solid fraction: 5.8% |
| Charge 4 | 10% IgG1/90% phenylalanine, solid fraction: 3.2% |
| Charge 5 | 10% IgG1/90% asparagine, solid fraction: 2.4% |
| Charge 6 | 10% IgG1/90% glycine, solid fraction: 11.18% |
| Charge 7 | 10% IgG1/90% isoleucine, solid fraction: 1.95% |
| Charge 8 | 10% IgG1/90% valine, solid fraction: 3.21% |
| Charge 9 | 10% IgG1/90% phenylalanine, solid fraction: 1.79% |
| Charge 10 | 10% IgG1/90% asparagine, solid fraction: 1.3% |

Figure 1A:
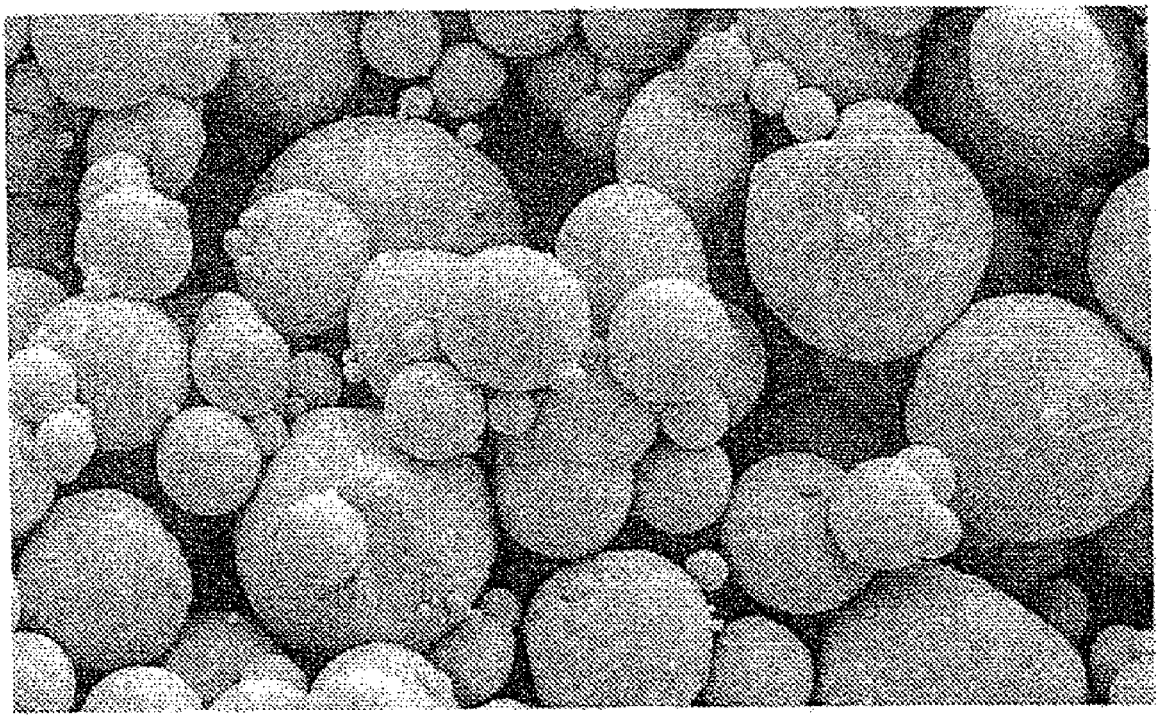
FIG. 1.
Figure 1B:
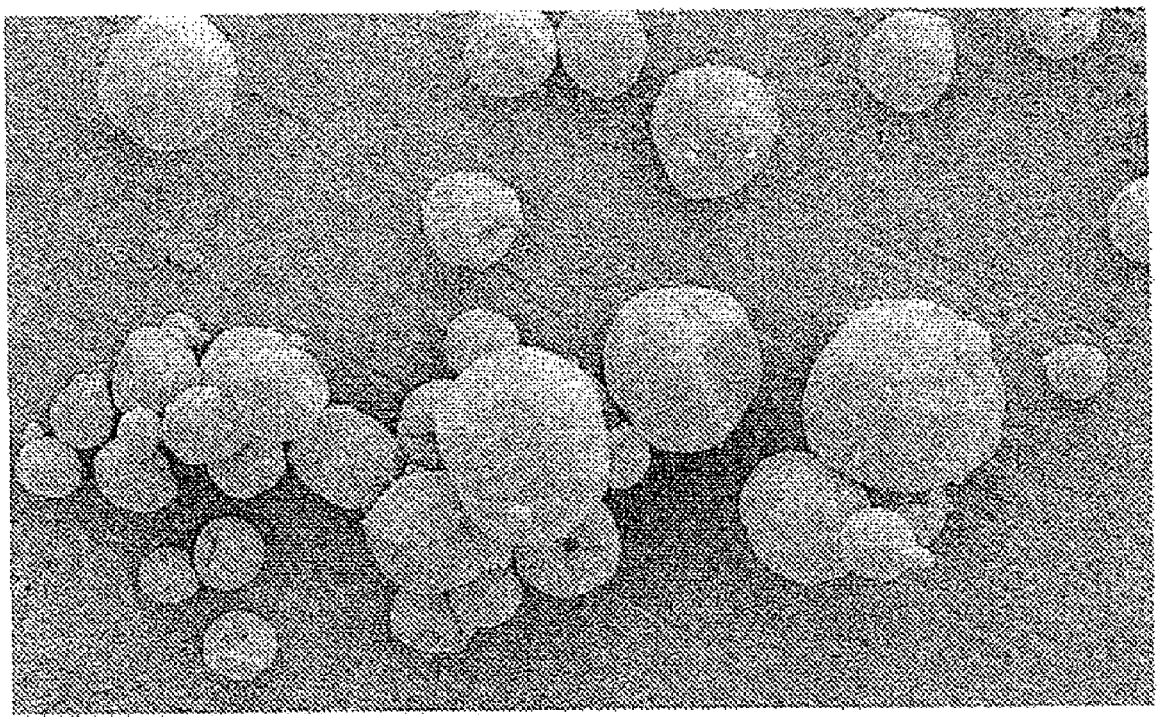
Figure 1C:
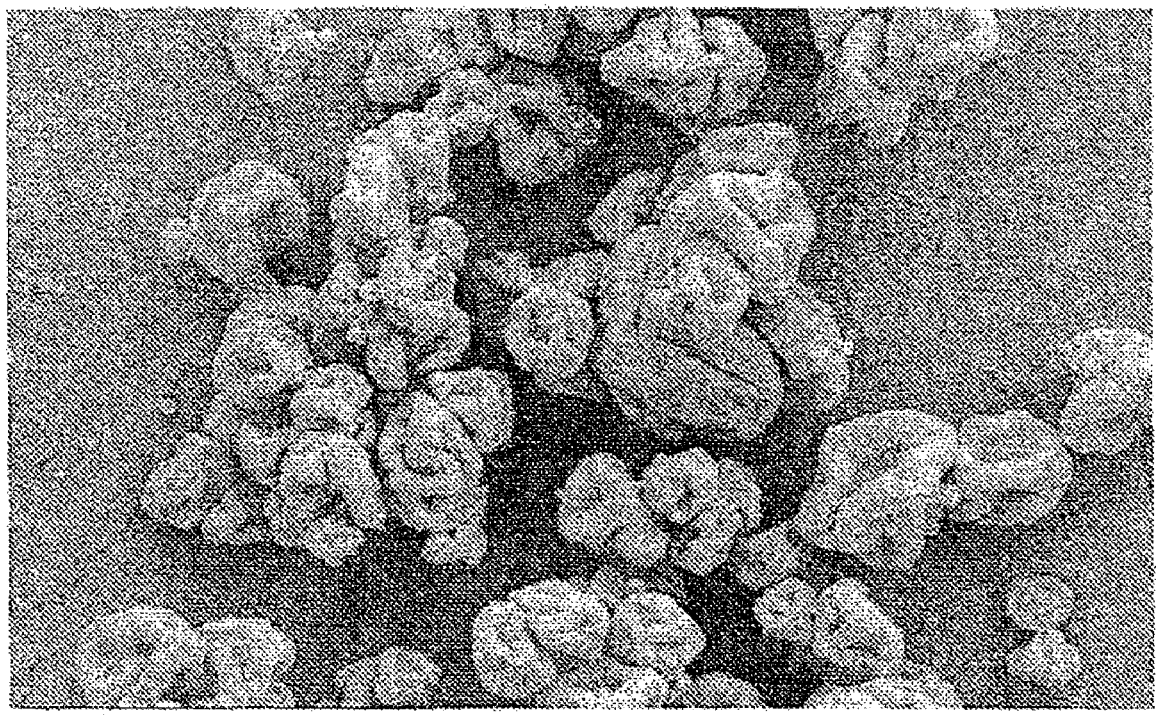
Figure 4:
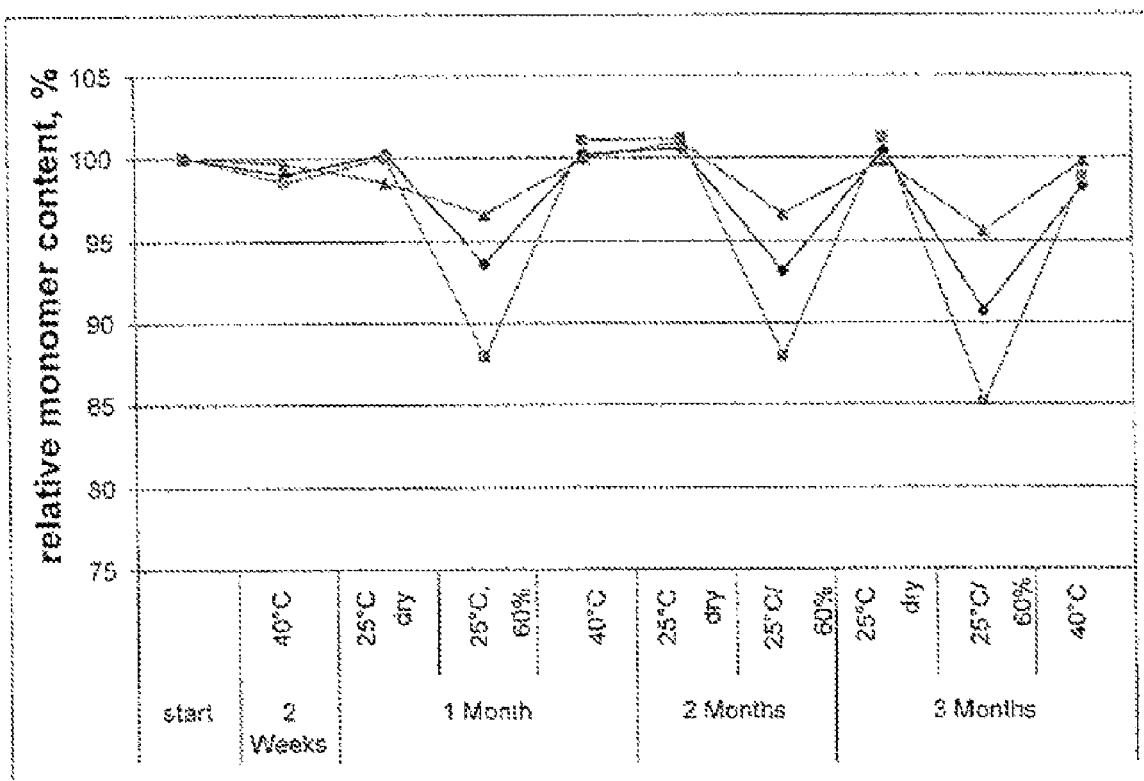

Bar: hydrophobicity of the amino acid
Diamond: Monomer content of the IgG1-antibody FIG. 3
SEM-Photographs of Different Ternary Powder Mixtures Containing Phenylalanine, Lactosucrose and an IgG1-Antibody The photographs were taken as described under FIG. 1.

a) Composition of the Spray-Dried Powder:
80% phenylalanine/10% LS90P/10% IgG1
magnification: 5000×
distance from powder to cathode: 9 mm
shutter size: 10 µm
acceleration voltage: 3 kV
vacuum: 1.72e-005 Pa b) Composition of the Spray-Dried Powder:
80% phenylalanine/15% LS90P/5% IgG1
magnification: 5000×
distance from powder to cathode: 7 mm
shutter size: 10 µm
acceleration voltage: 4 kV
vacuum: 9.18e-005 Pa c) Composition of the Spray-Dried Powder:
60% phenylalanine/30% LS90P/10% IgG1
magnification: 5000×
distance from powder to cathode: 8 mm
shutter size: 10 µm
acceleration voltage: 4 kV
vacuum: 9.18e-005 Pa d) Composition of the Spray-Dried Powder:
70% phenylalanine/25% LS90P/5% IgG1
magnification: 5000×
distance from powder to cathode: 8 mm
shutter size: 9 µm
acceleration voltage: 4 kV
vacuum: 9.3e-005 Pa FIG. 4
Relative Monomer Content Based on the Starting value. The monomer content was determined as described in FIG. 2. The relative monomer content is based on the starting value which is set at 100%. This Figure illustrates the change in the monomer content from the starting value and thus reflects the change over the storage time.

diamond: spray-dried powder: 60% phenylalanine/10% LS90P/30% IgG1
square: spray-dried powder: 80% phenylalanine/10% LS90P/10% IgG1
triangle: spray-dried powder: 60% phenylalanine/30% LS90P/10% IgG1

Figure 5:
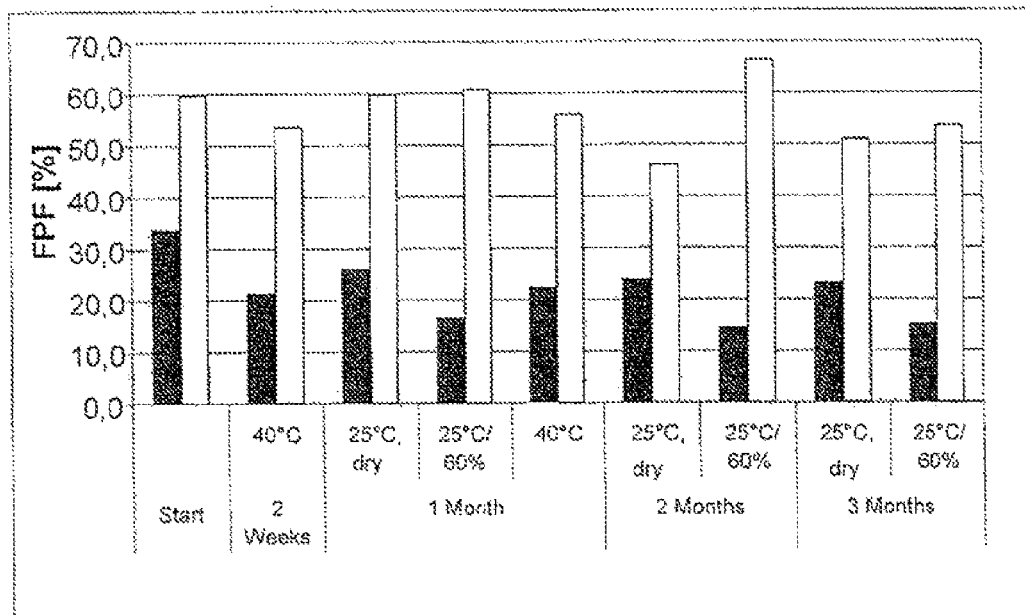
Figure 6:
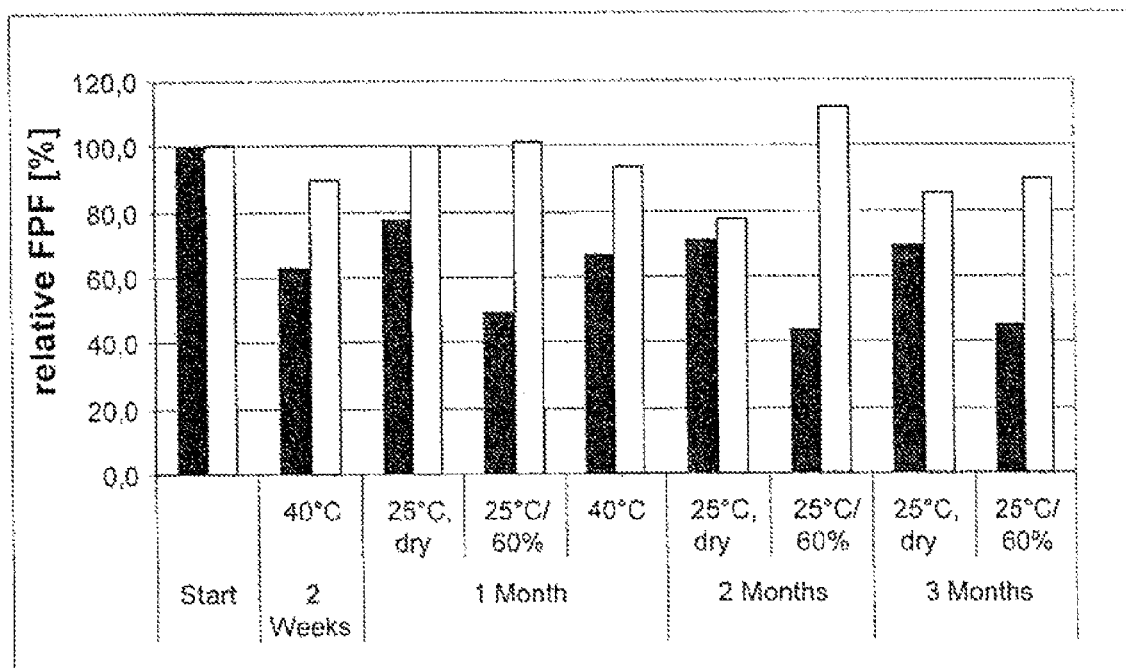
Figure 7A:
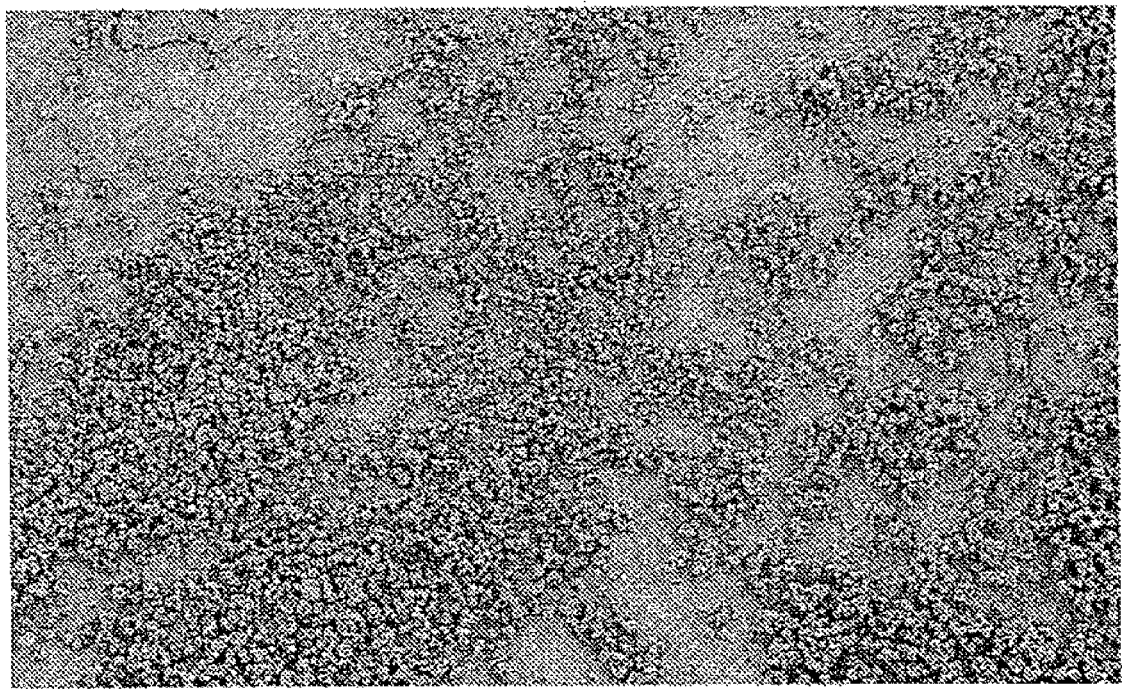
Figure 7B:
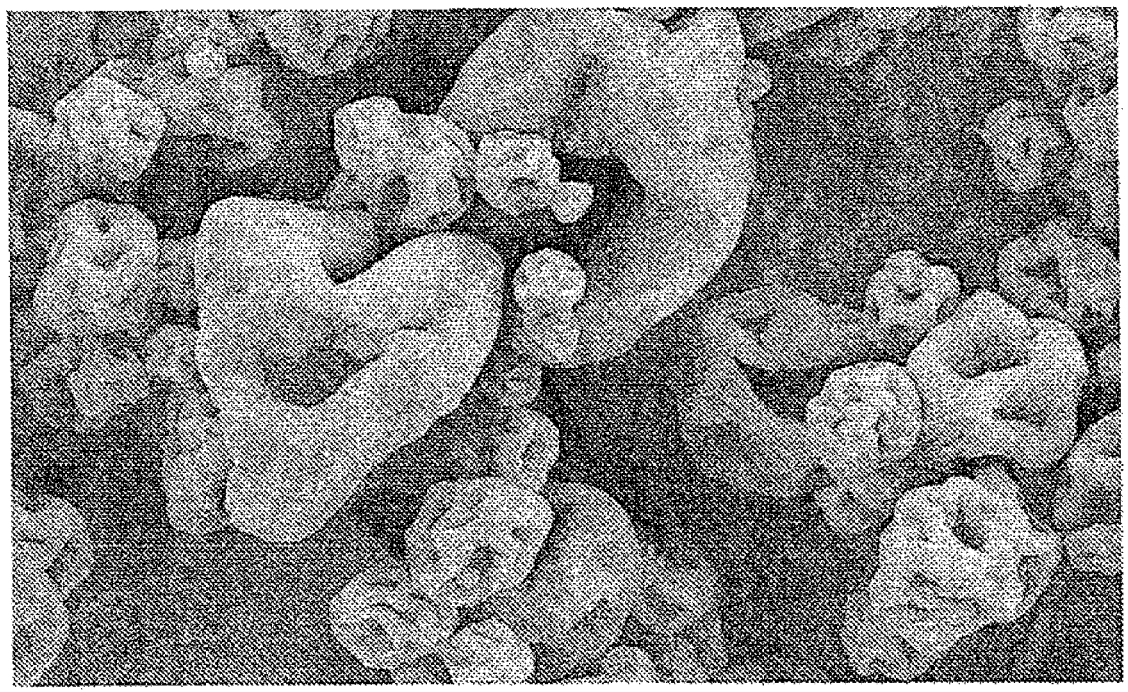
Figure 8A:
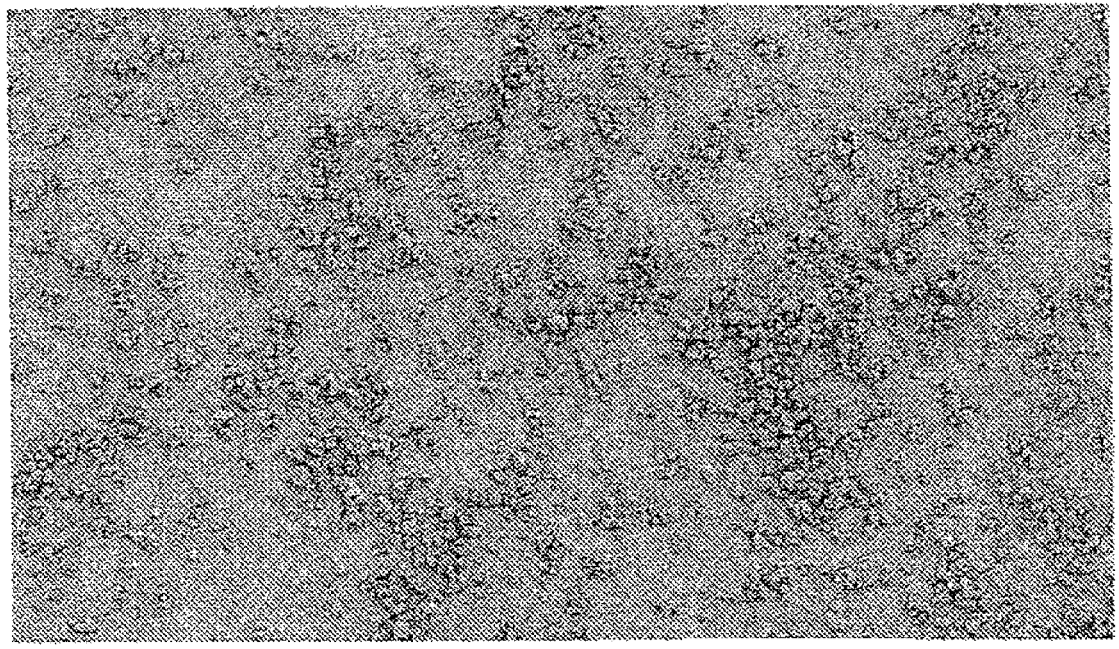
Figure 8B:
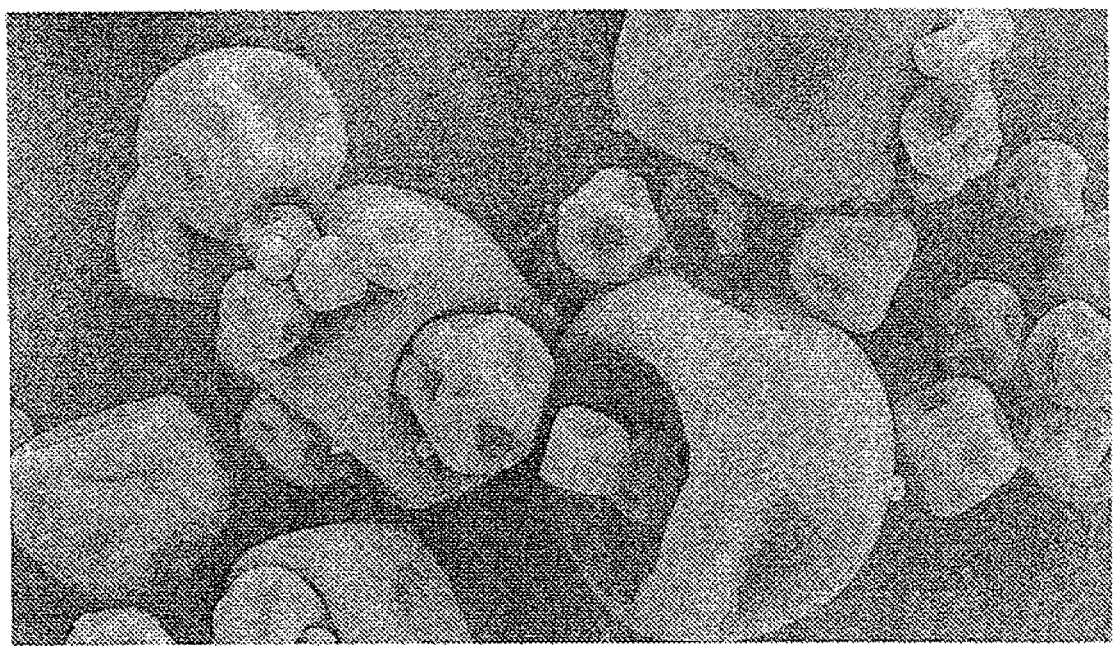

FIG. 5
Comparison of the fine particle fractions of various powder compositions. The fine particle fraction was determined using a one-stage impactor (Impactor Inlet, TSI) in combination with the Aerodynamic Particle Sizer (APS, TSI). The separation threshold of the impactor nozzle was 5.0 µm. In addition to the fine particle fraction the aerodynamic particle size was determined using the APS and the particle size distribution was determined by measuring the time of flight. To do this, the powder was split after passing through the Sample Induction Ports. A fraction of 0.2% was sucked into a small capillary under isokinetic conditions and the time of flight measuring unit was introduced. The remaining fraction was used to determine the fine particle fraction.

For measurement the powder was packed into size 3 capsules and expelled using an inhaler (HandiHaler®, Boehringer Ingelheim). The flow rate for expelling the powder was adjusted so that a pressure drop of 4 kPa prevailed through the HandiHaler. The air volume was 4 litres according to the PharmEur. To prevent "rebouncing" of the particles deposited on the impactor stage, the impactor plate has been coated with a highly viscous Brij solution for the measurements.

Dark bar: spray-dried powder: 65% dextran1/5% isoleucine/30% IgG1
Light bar: spray-dried powder: 60% phenylalanine/10% LS90P/30% IgG1

FIG. 6

Comparison of the relative fine particle fractions of various powder compositions. The relative fine particle fraction is based on the fine particle fraction of the starting value and thus reflects the change in the FPF over storage. The fine particle fraction is accordingly determined as in the description relating to FIG. 5.

Dark bar: spray-dried powder: 65% dextran1/5% isoleucine/30% IgG1
Light bar: spray-dried powder: 60% phenylalanine/10% LS90P/30% IgG1

FIG. 7

SEM photographs of spray-dried powders containing phenylalanine or isoleucine:
The photographs were taken as described under FIG. 1.
a) Composition of the Spray-Dried Powder:
60% phenylalanine/10% LS90P/10% IgG1
magnification: 250×
distance from powder to cathode: 7 mm
shutter size: 10 μm
acceleration voltage: 6 kV
vacuum: 5.35e-005 Pa
b) Composition of the Spray-Dried Powder:
60% phenylalanine/10% LS90P/10% IgG1
magnification: 5000×
distance from powder to cathode: 7 mm
shutter size: 10 μm
acceleration voltage: 6 kV
vacuum: 5.60e-005 Pa

FIG. 8

SEM Photographs of Spray-dried Powders Composed of 65% Dextran 1, 5% Isoleucine and 30% IgG1:
The photographs were taken as described under FIG. 1.
a) Composition of the Spray-Dried Powder:
65% dextran 1/5% isoleucine/30% IgG1
magnification: 250×
distance from powder to cathode: 9 mm
shutter size: 10 μm
acceleration voltage: 4 kV
vacuum: 6.70e-005 Pa
b) Composition of the Spray-Dried Powder:
65% dextran 1/5% isoleucine/30% IgG1
magnification: 7500×
distance from powder to cathode: 5 mm
shutter size: 10 μm
acceleration voltage: 5 kV
vacuum: 7.17e-005 Pa

FIG. 9

Determining the Fine Particle Fraction (FPF) and the Expelled Mass of Spray-Dried Powders Containing Various Proportions of Phenylalanine.

The fine particle fraction was determined with a one-stage impactor (Impactor Inlet, TSI) in combination with the Aerodynamic Particle Sizer (APS, TSI) (cf. also the description of FIG. 5). The expelled mass relates to the mass of the capsule used before and after expulsion through the Impactor Inlet/APS. The difference in the mass of the capsule corresponds to the expelled mass. The method of expulsion is described in Example 5.

Bars: fine particle fraction (FPF) in percent based on the weight in the capsule
Diamond: expelled mass of powder on delivery into the Impactor Inlet/TSI
Powder 1: Powder prepared by spray drying from a spray solution of the following composition: 0.29 g/100 mL phenylalanine, 1.15 g/100 mL IgG1, 383 mg/100 mL LS90P, buffer: 1.6 mM glycine, 25 mM histidine, pH 4.2
Powder 2: Powder prepared by spray drying from a spray solution of the following composition: 0.29 g/100 mL phenylalanine, 1.15 g/100 mL IgG1, 383 mg/100 mL LS90P, buffer: 25 mM TRIS, pH 7.4
Powder 3: Powder prepared by spray drying from a spray solution of the following composition: 0.29 g/100 mL phenylalanine, 1.15 g/100 mL IgG1, 383 mg/100 mL LS90P, buffer: 25 mM TRIS, pH 9.0

FIG. 10

SEM-Photographs of Spray-Dried Powders
The photographs were taken as described under FIG. 1.
a) Composition of the Spray-Dried Powder:
50% phenylalanine/20% LS90P/30% IgG1
magnification: 2000×
distance from powder to cathode: 10 mm
shutter size: 10 μm
acceleration voltage: 5 kV
vacuum: 2.23e-004 Pa
b) Composition of the Spray-Dried Powder:
40% phenylalanine/30% LS90P/30% IgG1
magnification: 3000×
distance from powder to cathode: 10 mm
shutter size: 10 μm
acceleration voltage: 5 kV
vacuum: 2.23e-004 Pa
c) Composition of the Spray-Dried Powder:
30% phenylalanine/40% LS90P/30% IgG1
magnification: 3000×
distance from powder to cathode: 10 mm
shutter size: 10 μm
acceleration voltage: 5 kV
vacuum: 2.23e-004 Pa
d) Composition of the Spray-Dried Powder:
20% phenylalanine/50% LS90P/30% IgG1
magnification: 3000×
distance from powder to cathode: 8 mm
shutter size: 10 μm
acceleration voltage: 5 kV
vacuum: 2.26e-004 Pa

FIG. 11

Determining the Fine Particle Fraction (FPF) and the Expelled Mass of Spray-dried Powders The fine particle fraction was determined with a one-stage impactor (Impactor Inlet, TSI) in combination with the Aerodynamic Particle Sizer (APS, TSI) (cf also on this subject the description of FIG. 5). The expelled mass relates to the mass of the capsule used before and after expulsion through the Impactor Inlet/APS. The difference in the mass of the capsule corresponds to the expelled mass. The method of expulsion is described in Example 5.

Bar: fine particle fraction (FPF) in percent based on the weight in the capsule
Diamond: expelled mass of powder on delivery into the Impactor Inlet/TSI
Powder 1: spray-dried powder: 60% phenylalanine, 10% IgG1, 30% LS90P
Powder 2: spray-dried powder: 60% phenylalanine, 10% lysozyme, 30% LS90P Powder 3: spray-dried powder: 60% phenylalanine, 10% calcitonin, 30% LS90P

FIG. 12

Determining the Fine Particle Fraction (FPF) and the Expelled Mass of Spray-Dried Powders The fine particle fraction was determined with a one-stage impactor (Impactor Inlet, TSI) in combination with the Aerodynamic Particle Sizer (APS, TSI) (cf also on this subject the description of FIG. 5). The expelled mass relates to the mass of the capsule used before and after expulsion through the Impactor Inlet/APS. The difference in the mass of the capsule corresponds to the expelled mass. The method of expulsion is described in Example 5.

Bar: fine particle fraction (FPF) in percent based on the weight in the capsule

Diamond: expelled mass of powder on delivery into the Impactor Inlet/TSI

Powder 1: spray-dried powder: 60% phenylalanine, 10% IgG1, 30% saccharose

Powder 2: spray-dried powder: 60% phenylalanine, 10% IgG1, 30% mannitol

Powder 3: spray-dried powder: 60% phenylalanine, 10% IgG1, 30% glycine

Powder 4: spray-dried powder: 60% phenylalanine, 10% IgG1, 30% PVP

FIG. 13

DSC Measurements for Determining the Crystallisation Enthalpy of the LS90P

The crystallisation enthalpy was determined by measuring the heat currents during the heating of the powders. When an amorphous powder is heating up the constituents of the particle have increased mobility after passing through the glass transition temperature and may crystallise. Passing through the glass transition temperature is an endothermic process. The subsequent crystallisation, on the other hand, is exothermic. As the powder is heated further it may melt or decompose.

For the DSC measurements, a few milligrams of powder were slightly compressed in a crucible so as to form a bed of powder that was as homogeneous and dense as possible. Then the crucible was sealed by cold welding. The measurements were carried out with an unperforated crucible.

The other parameters were:

| | |
|---|---|
| Measuring equipment: | DSC 821/Mettler Toledo |
| Evaluating software: | STAR version 4.20 |
| furnace gas: | nitrogen/40 mL/min |
| flushing gas: | nitrogen/150 mL/min |
| crucible: | aluminium crucible, 40 µL |
| scan rate: | temperature 10° C./min |

Powder 1: spray-dried powder: 60% phenylalanine/40% LS90P

Powder 2: spray-dried powder: 60% phenylalanine/30% LS90P/10% IgG1

Powder 3: spray-dried powder: 60% phenylalanine/30% LS90P/10% lysozyme

Powder 4: spray-dried powder: 60% phenylalanine/30% LS90P/10% calcitonin

Powder 5: freeze-dried powder: 100% LS90P

FIG. 14

Determining the Fine Particle Fraction (FPF) of Spray-Dried Powders

The fine particle fraction was determined with a one-stage impactor (Impactor Inlet, TSI) in combination with the Aerodynamic Particle Sizer (APS, TSI) (cf also on this subject the description of FIG. 5).

The expelled mass is obtained from the difference in weight of the capsule before and after the expulsion through the inhaler (HandiHaler®, Boehringer Ingelheim).

Empty bar: measurement of the FPF directly after spray drying

Dotted bar: measurement of the FPF after exposure to moisture (50% RH at ambient temperature over 20 hours)

triangles: expelled mass directly after spray drying rectangles: expelled mass after exposure to moisture (50% RH at ambient temperature over 20 hours)

Powder 1: spray-dried powder: 20% tryptophan/50% LS90P/30% IgG1

Powder 2: spray-dried powder: 20% histidine/50% LS90P/30% IgG1

Powder 3: spray-dried powder: 20% phenylalanine/50% LS90P/30% IgG1

DETAILED DESCRIPTION OF THE INVENTION

Definitions

Terms and designations used within the scope of this specification have the following meanings defined below. The details of weight and percentages by weight are based on the dry mass of the compositions or the solids content of the solutions/suspensions, unless stated otherwise.

The general expressions "containing" or "contains" include the more specific term of "consisting of". Moreover, "one" and "many" are not used restrictively.

"powders" denotes a very fine, comminuted substance. "Spray-dried powder" means a powder produced by spray drying.

"Particle" denotes a small fragment of a substance. In the present invention the term particles refers to the particles in the powders according to the invention.

The terms particles and powders are occasionally used interchangeably in the present invention. The term powder also includes its constituents, the particles. Particles thus refer to all the particles, i.e. the powder.

The term "mixture" or "mixtures" in the sense of this invention refers both to those mixtures which are generated from a genuine solution of all the components or from a solution in which one or more of the components have or has been suspended. However, the term "mixtures" in the sense of this invention also refers to mixtures which have been produced by a physical mixing process from solid particles of these components or which have formed by the application of a solution or suspension of these components to one or more solid components.

The term "composition" refers to liquid, semi-solid or solid mixtures of at least two starting materials.

The term "pharmaceutical composition" refers to a composition for administering to the patient.

The term "pharmaceutically acceptable excipients" relates to excipients, which may possibly be present in the formulation within the scope of the invention. The excipients may for example be administered by pulmonary route without having any significant toxicologically harmful effects on the subjects or on the subjects' lungs.

The term "pharmaceutically acceptable salts" includes for example the following salts, but is not restricted thereto: salts of inorganic acids such as chloride, sulphate, phosphate, diphosphate, bromide and nitrate salts. Also, salts of organic acids, such as malate, maleate, fumarate, tartrate, succinate, ethylsuccinate, citrate, acetate, lactate, methanesulphonate, benzoate, ascorbate, para-toluenesulphonate, palmoate, salicylate and stearate, and also estolate, gluceptate and lactobianate salts.

By the term "active substances" are meant substances that provoke an activity or a reaction in an organism. If an active substance is administered to a human or to an animal body for therapeutic purposes, it is referred to as a pharmaceutical composition or medicament.

By a "protein active substance" is meant in the present invention an active substance which is structurally present as a protein or structurally constitutes a protein, polypeptide or peptide.

Examples of active substances are insulin, insulin-like growth factor, human growth hormone (hGH) and other growth factors, tissue plasminogen activator (tPA), erythropoietin (EPO), cytokines, e.g. interleukines (IL) such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18 interferon (IFN)-alpha, -beta, -gamma, -omega or -tau, tumour necrosis factor (TNF) such as TNF-alpha, beta or gamma, TRAIL, G-CSF, GM-CSF, M-CSF, MCP-1 and VEGF. Other examples are monoclonal, polyclonal, multispecific and single chain antibodies and fragments thereof such as for example Fab, Fab', F(ab')$_2$, Fc and Fc' fragments, light (L) and heavy (H) immunoglobulin chains and the constant, variable or hypervariable regions thereof as well as Fv and Fd fragments (Chamov et al., 1999). The antibodies may be of human or non-human origin. Humanised and chimeric antibodies are also possible. Similarly, it relates to conjugated proteins and antibodies which are connected for example to a radioactive substance or a chemically defined medicament.

Fab fragments (fragment antigen binding=Fab) consist of the variable regions of both chains which are held together by the adjacent constant regions. They may be produced for example from conventional antibodies by treating with a protease such as papain or by DNA cloning. Other antibody fragments are F(ab')$_2$ fragments which can be produced by proteolytic digestion with pepsin.

By gene cloning it is also possible to prepare shortened antibody fragments which consist only of the variable regions of the heavy (VH) and light chain (VL). These are known as Fv fragments (fragment variable=fragment of the variable part). As covalent binding via the cystein groups of the constant chains is not possible in these Fv fragments, they are often stabilised by some other method. For this purpose the variable region of the heavy and light chains are often joined together by means of a short peptide fragment of about 10 to 30 amino acids, preferably 15 amino acids. This produces a single polypeptide chain in which VH and VL are joined together by a peptide linker. Such antibody fragments are also referred to as single chain Fv fragments (scFv). Examples of scFv antibodies are known and described, cf. for example Huston et al., 1988.

In past years various strategies have been developed for producing multimeric scFv derivatives. The intention is to produce recombinant antibodies with improved pharmacokinetic properties and increased binding avidity. In order to achieve the multimerisation of the scFv fragments they are produced as fusion proteins with multimerisation domains. The multimerisation domains may be, for example, the CH3 region of an IgG or helix structures ("coiled coil structures") such as the Leucine Zipper domains. In other strategies the interactions between the VH and VL regions of the scFv fragment are used for multimerisation (e.g. dia-, tri- and pentabodies).

The term diabody is used in the art to denote a bivalent homodimeric scFv derivative. Shortening the peptide linker in the scFv molecule to 5 to 10 amino acids results in the formation of homodimers by superimposing VH/VL chains. The diabodies may additionally be stabilised by inserted disulphite bridges. Examples of diabodies can be found in the literature, e.g. in Perisic et al., 1994.

The term minibody is used in the art to denote a bivalent homodimeric scFv derivative. It consists of a fusion protein which contains the CH3 region of an immunoglobulin, preferably IgG, most preferably IgG1, as dimerisation region. This connects the scFv fragments by means of a hinge region, also of IgG, and a linker region. Examples of such minibodies are described by Hu et al., 1996.

The term triabody is used in the art to denote a trivalent homotrimeric scFv derivative (Kortt et al., 1997). The direct fusion of VH-VL without the use of a linker sequence leads to the formation of trimers.

The fragments known in the art as mini antibodies which have a bi-, tri- or tetravalent structure are also derivatives of scFv fragments. The multimerisation is achieved by means of di-, tri- or tetrameric coiled coil structures (Pack et al., 1993 and 1995; Lovejoy et al., 1993).

The term "excipients" refers to substances which are added to a formulation, in the present invention a powder, particularly spray-dried powder. Excipients usually have no activity themselves, particularly no pharmaceutical activity, and serve to improve the formulation of the actual ingredient, e.g. an active substance, or to optimise a particular aspect thereof (e.g. storage stability).

A pharmaceutical "excipient" is a part of a medicament or a pharmaceutical composition, and ensures among other things that the active substance reaches the activity site and is released there. Excipients have three basic tasks: a carrier function, controlling the release of active substance and increasing the stability. Excipients are also used to produce pharmaceutical forms which are thereby altered in their duration or rate of effect.

The term "amino acid" refers to compounds which contain at least one amino and at least one carboxyl group. Although the amino group is usually in the α-position to the carboxyl group, any other arrangement in the molecule is conceivable. The amino acid may also contain other functional groups, such as e.g. amino, carboxamide, carboxyl, imidazole, thio groups and other groups. Amino acids of natural or synthetic origin, racemic or optically active (D- or L-) including various stereoisomeric proportions, may be used. For example the term isoleucine includes both D-isoleucine, L-isoleucine, racemic isoleucine and various ratios of the two enantiomers.

The term "peptide", "polypeptide" or "protein" refers to polymers of amino acids consisting of more than two amino acid groups.

The term peptide, polypeptide or protein is used as a pseudonym and includes both homo- and heteropeptides, i.e. polymers of amino acids consisting of identical or different amino acid groups. A "di-peptide" is thus made up of two peptidically linked amino acids, a "tri-peptide" is made up of three peptidically linked amino acids.

The term "small protein" refers to proteins under 50 kD or under 30 kD or between 5-50 kD. The term "small protein" further relates to polymers of amino acid groups with less than 500 amino acid groups or less than 300 amino acid groups or polymers with 50-500 amino acid groups. Preferred small proteins are e.g. growth factors such as "human growth hormone/factor", insulin, calcitonin or the like.

The term "oligosaccharide" or "polysaccharide" refers to polysaccharides consisting of at least three monomeric sugar molecules.

The term "% (w/w)" refers to the percentage amount, based on the mass, of an active substance or an excipient in the spray-dried powder. The proportion stated is based on the dry substance of the powder. The residual moisture in the powder is thus not taken into consideration.

The term "amorphous" means that the powdered formulation contains less than 10% crystalline fractions, preferably less than 7%, more preferably less than 5%, and most preferably less than 4, 3, 2, or 1%.

The word "inhalable" means that the powders are suitable for pulmonary administration. Inhalable powders can be dispersed and inhaled by means of an inhaler so that the particles enter the lungs and are able to develop a systemic activity optionally through the alveoli. Inhalable particles may have an average particle diameter, for example, of between 0.4-30 µm (MMD=mass medium diameter), usually between 0.5-20 µm, preferably between 1-10 µm and/or an average aerodynamic particle diameter (MMAD=mass median aerodynamic diameter) of between 0.5-10 µm, preferably between 0.5-7.5 µm, more preferably between 0.5-5.5 µm, even more preferably between 1-5 µm and most preferably between 1-4.5 µm or 3-10 µm.

"Mass Median Diameter" or "MMD" is a measurement of the average particle size distribution as the powders according to the invention are generally polydispersed. The results are expressed as diameters of the total volume distribution at 50% total throughflow. The MMD values can be determined for example by laser diffractometry, although of course any other conventional method may be used (e.g. electron microscopy, centrifugal sedimentation).

The term "mean aerodynamic particle diameter" (=mass median aerodynamic diameter (MMAD)) indicates the aerodynamic particle size at which 50% of the particles based on the mass of the powder normally have a smaller aerodynamic diameter. In cases of doubt the reference method for determining the MMAD is the method specified in this patent specification.

MMD and MMAD may differ from one another, e.g. a hollow sphere produced by spray drying may have a greater MMD than its MMAD.

The term "fine particle fraction" (FPF) describes the inhalable part of a powder consisting of particles with a particle size of ≦5 µm MMAD. In powder which is readily dispersible the FPF is more than 20%, preferably more than 30%, more particularly more than 40%, and more preferably more than 50%, even more preferably more than 55%. The expression "Cut Off Diameter" used in this context indicates which particles are taken into account when determining the FPF. An FPF of 30% with a Cut Off Diameter of 5 µm ($FPF_5$) means that at least 30% of all the particles in the powder have a mean aerodynamic particle diameter of less than 5 µm.

The term "time of flight" is the name of a standard method of measurements, as described in more detail in the Chapter EXAMPLES. In a time of flight measurement the MMAD is determined by measuring the time of flight of a particle over a defined measured distance. The MMAD correlates with the time of flight/This means that particles with a greater MMAD take a longer time to fly than correspondingly smaller particles (cf. one this subject: Chapter EXAMPLES, Method).

The term "expelled mass" states the amount of powder delivered when an inhaler is used. The delivery is determined in this case for example using a capsule, by weighing the capsule before and after the expulsion. The expelled mass corresponds to the difference in mass of the capsule before and after the expulsion.

The term "dispersible" means capable of flight. The basic prerequisite for the ability of a powder to fly is the disaggregation of the powder into individual particles and the distribution of the individual particles in air. Particle clumps are too big to enter the lungs and are therefore not suitable for inhalation therapy.

The term "ambient temperature" denotes a temperature of approx. 20-25° C. (+/−10%). The term ambient temperature denotes in particular a temperature of 25° C.

The term "monomer content" and "monomer" denotes the percentage proportion of protein consisting of a single subunit of the protein. A distinction must be drawn between the monomer content and fractions consisting of small fragments of the monomer and di- or oligomers consisting of several subunits. The monomer content is determined for example by exclusion chromatography.

The term "aggregates" refers to the proportion of di- and oligomers of proteins that consist of a single subunit in the native state.

Compositions According to the Invention

The factors that determine the flight characteristics of the spray-dried particles (fine particle fraction FPF is relevant here) are the size of the particles (MMD or particularly MMAD, which is determined by time-of-flight measurements) and the dispersion characteristics of the powders. The chemical composition of the particle surface and the morphology of the particles are crucial to the dispersion characteristics of the powders. Accordingly, the dispersion characteristics of the powders can be decisively influenced by the deliberate choice of the powder constituents and particularly the excipients.

The size and morphology of a particle are obtained on drying an individual drop after atomisation in the spray dryer, as follows:

Inhalable powders are usually produced using two-substance nozzles. The droplet size (MMD), which is relevant as the starting point for the later particle size, is about 8-20 µm, depending on the rate of the atomiser gas. The drop is dried over 2 steps. In the first phase water is evaporated without any solid being formed. The evaporation is not diffusion-limited. After the solubility limit of a substance contained in the solution is reached a solid/liquid dual phase develops and finally a sealed solid layer is formed. The nucleus of the particle forming also contains water and dissolved substances with a correspondingly higher solubility limit than the substance that has already precipitated.

The second phase of the particle formation begins after the formation of the sealed solid layer. The evaporation rate of the water is sharply reduced by the solid layer. In the 2nd phase the evaporation rate of the water depends on the rate of diffusion of the water through the particle layer. If the vapour diffusion is seriously inhibited, the rise in the temperature in the nucleus of the particle that is forming causes elevated vapour pressure. To balance this out, the particles inflate, thus forming hollow spheres. After evaporation of the water or during the cooling of the particle, a reduced pressure is formed in the nucleus of the particle. Depending on the stability of the particle layer, either the particle solidifies in the inflated form or the particle collapses.

The tendency of the particles to collapse depends not only on a size of substance or process. Rather, it is a complex function of the hydrophobicity of the solids, the solubility limit reached and the solid fraction of the spray solution. The combination of solubility limit and solid fraction of the spray solution also controls the thickness of the particle layer. Other influencing variables such as e.g. the glass transition temperature and, derived from it, the viscosity of the powder in the spray dryer could also influence the tendency to collapse.

To summarise, it can be stated roughly speaking that the tendency of the nascent particles to inflate increases with the hydrophobicity and the decreasing solubility of the excipients. The tendency to collapse of the inflated particles on the other hand appears to be a substance-specific property. It has been shown that in this context phenylalanine brings about a surprisingly good and unexpected morphology of the powder, particularly in protein-containing powders and spray-dried powders. This effect is particularly advantageous for the inhalation of such powders.

Excipients of similar hydrophobicity or solubility (valine, isoleucine) exhibited no comparable morphology and hence no comparable aerodynamic characteristics.

The present invention relates to powders containing a protein and phenylalanine, characterised in that the powder contains at least 30% (w/w) phenylalanine (at least binary complex).

The invention relates particularly to a powder containing a protein, phenylalanine and at least one other excipient such as a sugar or a polyol, characterised in that the powder contains at least 30% (w/w) phenylalanine (at least ternary complex).

The present invention relates to powders containing a protein and phenylalanine, characterised in that the powder contains at least 40% (w/w) phenylalanine (at least binary complex).

The invention relates particularly to a powder containing a protein, phenylalanine and at least one further excipient such as a sugar or a polyol, characterised in that the powder contains at least 40% (w/w) phenylalanine (at least ternary complex).

In a preferred embodiment the present powder (at least binary or at least ternary) is a spray-dried powder.

In a special embodiment the invention relates to powders containing a protein or a protein-active substance and phenylalanine as excipient and optionally a further excipient such as a sugar or a polyol, while the powder is characterised in that it contains at least 30% (w/w) phenylalanine, preferably at least 40% (w/w) phenylalanine. Optionally other substances particularly other excipients may be contained in the powder. Furthermore this special embodiment of the present invention also relates to a pharmaceutical composition which contains a powder, consisting of a protein or a protein-active substance and phenylalanine as excipient and optionally a further excipient such as a sugar or a polyol, while the powder consists of at least 30% (w/w) phenylalanine, preferably at least 40% (w/w) phenylalanine.

In a further embodiment the present powder contains at least 30% (w/w), 31% (w/w), 32 (w/w), 33 (w/w), 34 (w/w), 35 (w/w), 36 (w/w), 37 (w/w), 38 (w/w), 39 (w/w), 40% (w/w), 41% (w/w), 42% (w/w), 43% (w/w), 44% (w/w), 45% (w/w), 46% (w/w), 47% (w/w), 48% (w/w), 49% (w/w), 50% (w/w), 51% (w/w), 52% (w/w), 53% (w/w), 54% (w/w), 55% (w/w), 56% (w/w), 57% (w/w), 58% (w/w), 59% (w/w), 60% (w/w), 61% (w/w), 62% (w/w), 63% (w/w), 64% (w/w), 65% (w/w), 66% (w/w), 67% (w/w), 68% (w/w), 69% (w/w), 70% (w/w), 75% (w/w), 80% (w/w), 85% (w/w), 90% (w/w), 95% (w/w), 99% (w/w) or 99.99% (w/w) phenylalanine. High percentages of phenylalanine are particularly preferred in highly potent proteins such as cytokines and interferons (IFN-alpha, IFN-beta, IFN-gamma, IFN-omega, pegylated IFN etc.), as only small amounts of this protein are needed (0.01% (w/w) to 10% (w/w), particularly 0.01% (w/w) to 5% (w/w) and particularly 0.01% (w/w) to 1% (w/w)).

In a preferred embodiment the present powder contains a proportion of phenylalanine in the region of 30% (w/w) to 99.99% (w/w), preferably 40% (w/w) to 99.99% (w/w), preferably 40% (w/w) to 70% (w/w), 60%-90% or particularly preferably 60% to 80%.

In a further embodiment the present powder contains a non-reducing sugar selected from among a disaccharide and an oligosaccharide. Preferably the disaccharide is saccharose or trehalose, the oligosaccharide is a trisaccharide such as for example lactosucrose.

In another embodiment the proportion of sugar is at most 50% (w/w), preferably 5, 10, 15, 20, 25, 30, 35, 40, 45% (w/w) and particularly preferably 10 to 20% (w/w).

In a further embodiment the present powder contains a polyol. Preferably the polyol is mannitol.

In a further embodiment the mass ratio of sugar to protein is between 1:10 to 10:1, preferably 1:3 to 5:1.

In a further preferred embodiment the present powder contains a crystallisation inhibitor such as HSA (human serum albumin) Preferably the powder contains at least 0.1% (w/w) HSA, at least 0.5% (w/w) HSA, at least 1% (w/w) HSA, at least 5% (w/w) HSA, at least 10% (w/w) HSA, at least 15% (w/w) HSA. Furthermore the powder preferably contains between 0.1% (w/w)-60% (w/w) HSA, 0.5% (w/w)-60% (w/w) HSA, 1% (w/w)-60% (w/w) HSA, 10% (w/w)-60% (w/w) HSA, 0.1% (w/w)-40% (w/w) HSA, 0.5% (w/w)-40% (w/w) HSA, 1% (w/w)-40% (w/w) HSA, 10% (w/w)-40% (w/w) HSA, 0.1% (w/w)-20% (w/w) HSA, 0.5% (w/w)-20% (w/w) HSA, 1% (w/w)-20% (w/w) HSA, 10% (w/w)-20% (w/w) HSA, 0.1% (w/w)-1% (w/w) HSA, 0.5% (w/w)-1% (w/w) HSA, 0.1% (w/w)-0.90% (w/w) HSA, 0.5% (w/w)-0.9% (w/w) HSA, 0.1% (w/w)-3% (w/w) HSA, 0.5% (w/w)-3% (w/w) HSA. Furthermore the powder preferably contains less than 1% (w/w) HSA, less than 0.9% (w/w) HSA.

In a further preferred embodiment the present powder has a pH of >6.0, >6.5, >7.0, >7.4, >8. A pH range of between 6.0 to 9.0 or 7.0 to 8.0 is particularly preferred.

In a further particularly preferred embodiment the present powder is at a physiological pH. In a further particularly preferred embodiment the present powder is at pH 7.0 to 7.4. In a further preferred embodiment the present powder is at a pH which does not correspond to the isoelectric point of phenylalanine.

In a preferred embodiment the protein is an active substance, preferably a pharmaceutical active substance such as for example an antibody, an antibody fragment, a fusion protein with parts of antibodies or a conjugated antibody, a growth factor, a hormone, an enzyme, a cytokine or an interferon. In a particularly preferred embodiment the pharmaceutical active substance is insulin or calcitonin.

In a further embodiment the pharmaceutical active substance is a fusion protein or an antibody fragment that binds to the neonatal Fc-receptor.

In a further embodiment the protein content is 0.01-70% (w/w), 0.01-60% (w/w), 0.01-50% (w/w), 0.01-40% (w/w), 1-50% (w/w), 10-50% (w/w) and preferably 30-50% (w/w).

In a preferred embodiment the ratio of phenylalanine/sugar/protein is 40/10/50, 99.89/0.1/0.01, 90/9/1, 90/1/9, 80/10/10, 30/10/60, preferably 60/10/30 or 50/10/40.

In a particularly preferred embodiment the powder consists of phenylalanine/lactosucrose or saccharose/and a small protein in a ratio by mass of 60/10/30.

In a further embodiment the mean aerodynamic particle size (MMAD=mass median aerodynamic diameter) of the powder particles is less than 10 μm, preferably less than 7.5, even more preferably in the range between 1-6 μm or 3-6 μm or 5-7 μm.

In a further embodiment the invention relates to a pharmaceutical composition, which contains the powder according to the invention.

In a further embodiment the pharmaceutical composition further contains pharmaceutically acceptable excipients or pharmaceutically acceptable excipients such as pharmaceutically acceptable salts, buffer, detergents and the like.

The present invention further relates to a process for preparing a powder according to the invention, wherein
a) a phenylalanine solution is prepared,
b) at least one protein and optionally at least one further excipient such as a sugar or a polyol are added,
c) the solution or suspension thus obtained is sprayed at an inflow temperature of preferably 90-200° C. and an outflow temperature of preferably 40-150° C. and
d) the particles formed are separated from the drying gas.

In a preferred embodiment of the method according to the invention the solvent is water, ethanol, isopropanol etc.

In a particularly preferred embodiment of the present method the protein is a pharmaceutical active substance. The pharmaceutical active substance is preferably a small protein, an antibody, an antibody fragment, a fusion protein with parts of antibodies or a conjugated antibody, a growth factor, a hormone, an enzyme, a cytokine or an interferon. In a particularly preferred embodiment the pharmaceutical active substance is insulin, calcitonin. In a further most particularly preferred embodiment the pharmaceutical active substance is an antibody of class IgG1, IgG2 IgG3, IgG4, an antibody fragment, an interferon or the like.

In a further preferred embodiment of the present method in step b) first of all the further excipient such as a sugar or a polyol is added followed by the active substance.

In a further embodiment of the present method the following steps are carried out between step a) and b)
heating of the phenylalanine solution, preferably to 80° C.,
cooling of the phenylalanine solution to below the denaturing temperature of the particular protein which is to be added in each case, the cooling preferably being to ambient temperature.

In a preferred embodiment of the present method the solution or suspension is sprayed in step c) by means of at least one pressure nozzle or at least one rotary evaporator or at least one venturi nozzle or at least one ultrasound nebuliser or at least one two-substance nozzle. In a particularly preferred embodiment the solution or suspension is sprayed in step c) using at least one two-substance nozzle.

In a further preferred embodiment of the present method the separation of the particles in step d) is carried out using at least one particle separator, preferably at least one cyclone.

The present invention further relates to the use of a powder according to the invention or a pharmaceutical composition according to the invention as the medicament (1st medical indication).

In a preferred medicinal use the medicament contains a spray-dried powder according to the invention.

The present invention further relates to the use of a powder according to the invention or a pharmaceutical composition according to the invention as an inhaled medicament.

In a preferred medicinal use the inhalative pharmaceutical composition contains a spray-dried powder according to the invention.

The invention further relates to the use of a powder according to the invention or of a pharmaceutical composition according to the invention for preparing a medicament for the treatment of respiratory complaints or systemic diseases (2nd med. indication).

In a preferred embodiment the powder according to the invention used to prepare a medicament for the treatment of respiratory complaints or systemic diseases or the pharmaceutical composition used according to the invention is spray-dried.

In a particularly preferred embodiment the respiratory disease or systemic disease is selected from among lung cancer, inflammation of the lung, cystic fibrosis, COPD (chronic obstructive pulmonary disease), asthma, anti-inflammatory diseases, viral diseases e.g. caused by respiratory-syncytial virus (RSV).

A preferred embodiment of the present invention relates to an inventive powder, preferably a spray-dried powder, which contains no added magnesium stearate. Magnesium stearate is unsuitable for rendering particle surfaces hydrophobic by spray drying, as this substance is virtually insoluble in water and accordingly magnesium stearate suspensions would have to be used. In this case relatively high magnesium stearate concentrations are necessary to guarantee the desired particle coating. More suitable methods are therefore separate process steps, e.g. mixing the (spray-dried) powder with magnesium stearate.

In a further preferred embodiment the inventive powder, which is preferably spray-dried, or the inventive pharmaceutical composition contains no amino acids in addition to phenylalanine. The (spray-dried) powder also preferably contains exclusively the amino acid phenylalanine. This embodiment is preferred as other amino acids reduce or dilute the surprising aerodynamic effect of the phenylalanine.

Another preferred embodiment of the present invention relates to an inventive powder, preferably a spray-dried powder, which contains no added valine. The preferred powder is free from valine.

Another preferred embodiment of the present invention relates to an inventive powder, preferably a spray-dried powder, which contains no added isoleucine. The preferred powder is free from isoleucine.

Another preferred embodiment of the present invention relates to an inventive powder, preferably a spray-dried powder, which contains no added leucine. The preferred powder is free from leucine.

In a further preferred embodiment the powder, which is preferably spray-dried, contains no added surfactants such as Tween 20. This embodiment is preferred, as surfactants tend to have a destabilising effect on protein powders, particularly spray-dried protein powders.

Another preferred embodiment of the present invention relates to an inventive powder, preferably a spray-dried powder, which contains no added dextran. The preferred powder is free from dextran. Dextran-containing powders have impaired dispersibility and are therefore less preferable.

It is clear from the following experiments that the more hydrophobic amino acids cause the particles to inflate. The tendency to collapse as a function of the amino acids contained therein, on the other hand, is not predictable and does not follow any structurally based law. In the following Examples the tendency to collapse surprisingly increases in the order valine, isoleucine, phenylalanine. Whereas valine forms round particles, phenylalanine-containing particles are almost totally collapsed. The phenylalanine-containing powder has surprisingly extremely good aerodynamic properties. Fine particle fractions (FPF) of 65-72% may be achieved, regardless of the degree of saturation of the amino acid.

It should also be stressed that the maximum FPF achieved with the phenylalanine-containing powders is very high compared with powders, particularly spray-dried powders, that contain not phenylalanine but other excipients. The maximum achievable FPF is shown by the comparison of the FPF determined by the impactor stage and the proportion below 5 µm determined by measuring the time of flight. According to this, for readily dispersible powders, there is only a slight discrepancy between the FPF of the impactor stage and the fraction<5 µm determined by time of flight measurement.

With poorly dispersible powders on the other hand it is apparent that the FPF that can be obtained via the impactor stage is substantially smaller. The reason for this is that in the impactor process the fine particle fraction is determined over all the fractions. This means that the losses caused by powder remaining in the capsule, in the inhaler and in the sample induction port, for example, reduce the FPF determined. With the time of flight measurement on the other hand the balance is obtained solely through the powder that has already dispersed, which means that the losses described above do not come into the measurements.

It is to be assumed that the aerodynamic characteristics of the particles are heavily dependent on the particle morphology and the surface nature. Accordingly, multiple indentations in the particles or greatly collapsed particles, as in the case of phenylalanine-containing particles, are ideal for inhalation.

The collapsing and the associated non-uniform shape weaken the Van-der-Waals forces. In addition, the phenylalanine-containing particles, unlike the valine- and isoleucine-containing particles, have a substantially rougher surface structure. The rough surface structure could have been caused by crystallisation.

In the following Examples it was possible to show that phenylalanine on its own and particularly in conjunction with a sugar gives rise to very good aerodynamic properties of powders, particularly after spray drying. Phenylalanine on its own however is not capable of stabilising every protein, e.g. the IgG1-antibodies used in Examples 1 and 2. For such proteins, however, stabilisation by the addition of sugar is possible.

The Examples show that the protein can be stored under dry storage conditions both at 25° C. and at 40° C. over the tested storage periods of 1 month, 2 months and 3 months in almost totally stable condition. Under moist conditions there may be slight damage to the protein as in the antibody used in the Example.

The following Examples also show that the phenylalanine-containing powder has a substantially better FPF compared with a dextran-containing powder (59.6% as against 33.7%). As the aerodynamic particle sizes of the two powders are only slightly different or the phenylalanine-containing powder even has a slightly higher MMAD, the differences in the FPF can be put down to the dispersion characteristics of the powders as they are expelled from the capsule. This means that the phenylalanine-containing powder can be dispersed substantially better and hence interparticulate interactions are reduced, compared with the corresponding dextran-containing powders.

The Examples also show that compared with a dextran-containing powder the phenylalanine-containing powder has substantially smaller collapses in the FPF over the storage period. Phenylalanine is particularly advantageous at higher humidities (e.g. 25° C./60% relative humidity). Whereas in dextran-containing powder the FPF falls to 45-49% of the initial value, the phenylalanine-containing powder even shows an increase in the FPF after 2 months' storage at 25° C./60% relative humidity and after 3 months only a slight drop to 89% of the starting value.

The results of the Examples particularly underline the suitability of the ternary powder compositions at elevated humidities. The conventional powders, particularly spray-dried powders, generally show a major collapse in their aerodynamic characteristics on exposure to high humidities. Phenylalanine on the other hand, when stored at high humidities (e.g. 60% relative humidity), results in a stabilisation of the aerodynamics or, as shown in the Examples, even an improvement in them.

Morphology of the Powders:

As illustrated by the following Examples, neither powder, neither phenylalanine-containing powder nor dextran-containing powder, contains any large agglomerations of powder. Moreover multiple indentations can be seen in the formulations. An essential difference between the two morphologies is the higher surface roughness of the phenylalanine-containing powder. This increased surface roughness is presumably also the reason for the better dispersion characteristics.

The following Examples are provided to illustrate the present invention, and should not be construed as limiting thereof. All references cited herein are incorporated by reference in the application in their entireties.

EXAMPLES

Example 1

Binary Complexes

Binary solutions were prepared from an IgG1 and various amino acids which differed in their solubility and hydrophobicity. The concentration of amino acid in the spray solution was 50% with the amino acids used and in another test series it was 90% of the maximum achievable concentration of the particular amino acid (cf. Table 1). The mass ratio between IgG1 and amino acid was 95/5. As a result of the different solubilities of the amino acids correspondingly different solid fractions were obtained.

TABLE 1

Binary solutions of IgG1 and excipient

| Charge | protein | excipient | AA saturation level | proportion of solids, % |
|---|---|---|---|---|
| 1 | IgG1 | isoleucine | 90% | 3.5 |
| 2 | IgG 1 | glycine | 90% | 20.2 |
| 3 | IgG 1 | valine | 90% | 5.8 |
| 4 | IgG 1 | phenylalanine | 90% | 3.2 |
| 5 | IgG 1 | asparagine | 90% | 2.4 |
| 6 | IgG 1 | glycine | 50% | 11.18 |
| 7 | IgG 1 | isoleucine | 50% | 1.95 |
| 8 | IgG 1 | valine | 50% | 3.21 |
| 9 | IgG 1 | phenylalanine | 50% | 1.79 |
| 10 | IgG1 | asparagine | 50% | 1.3 |

The solutions were spray-dried under the following spray conditions:

| | |
|---|---|
| spray dryer: | SD-Micro (Messrs. Niro) |
| entry temperature | 120° C. |
| exit temperature: | 90° C. |
| atomiser gas rate: | 5 kg/h |
| drying gas rate: | 28 kg/h |

It was found that the more hydrophobic amino acids cause the particles to inflate. The tendency to collapse increased in the order valine, isoleucine and phenylalanine. Whereas valine formed round particles, phenylalanine was almost completely collapsed (cf. FIG. 1a-1c). The phenylalanine-containing powder had surprisingly extremely good aerodynamic properties. It was possible to achieve fine particle fractions (FPF) of 65-72% independently of the degree of saturation of the amino acid (cf. Table 2).

It should also be emphasised that the maximum achievable FPF with the phenylalanine-containing powders is very high compared with spray-dried powders having the excipients listed in Table 1. The maximum achievable FPF is obtained by comparing the FPF determined by the impactor stage and the proportion below 5 μm determined by measuring the time of flight. The APS method is explained in detail in the description of FIG. 5/6. According to this, for readily dispersible powders, there is only a slight discrepancy between the FPF of the impactor stage and the fraction below 5 μm determined by measuring the time of flight. In the case of poorly dispersible powders, on the other hand, it is apparent that the FPF obtained via the impactor stage is substantially smaller. The reason for this is that in the impactor method the fine particle fraction is determined over all the fractions. This means that the losses caused by powder remaining in the capsule, in the inhaler and in the sample induction port, for example, reduce the FPF determined. With the time of flight measurement on the other hand the balance is obtained solely through the powder that has already dispersed, which means that the losses described above do not come into the measurements.

It is to be assumed that the aerodynamic characteristics of the particles are heavily dependent on the particle morphology and the nature of their surface.

Accordingly, multiple indentations in the particles or greatly collapsed particles, as in the case of phenylalanine-containing particles, are ideal for inhalation.

The collapsing and the associated non-uniform shape weaken the Van-der-Waals forces. In addition, the phenylalanine-containing particles, unlike the valine- and isoleucine-containing particles, have a substantially rougher surface structure.

The rough surface structure could have been caused by crystallisation.

TABLE 2

Aerodynamic characteristics of the spray-dried powders, measured with the Aerodynamic Particle Sizer with Impactor Inlet

| excipient | MMAD$^a$ | proportion of particles < 5.0 μm, %$^a$ | FPF, %$^b$ | degree of achieving the max. FPF, %$^c$ |
|---|---|---|---|---|
| glycine (90%) | 4.94 | 55 | 24.6 | 45 |
| glycine (50%) | 4.24 | 70 | 32.7 | 47 |
| isoleucine (90%) | 2.06 | 89 | 59 | 66 |
| isoleucine (50%) | 1.97 | 86 | 55.1 | 64 |
| asparagine (90%) | 2.76 | 94 | 28.7 | 31 |
| asparagine (50%) | 2.77 | 87 | 14.7 | 17 |
| valine (90%) | 2.38 | 96 | 27.4 | 29 |
| valine (50%) | 2.26 | 98 | 28.4 | 29 |
| phenylalanine (90%) | 2.85 | 82 | 64.6 | 79 |
| phenylalanine (50%) | 2.6 | 91 | 71.8 | 79 |

$^a$the MMAD was determined using a time-of-flight measurement (TOF). For this the powder is expelled using the HandiHaler at a flow rate of 39.0 L/min through a Sample Induction Port (SIP). After passing through the SIP the powder aerosol is split. A fraction of 99.8% of the particle population is passed through a one-stage impactor. A fraction of 0.2% passes through a capillary into the TOF measuring cell.
$^b$The FPF is determined using a one-stage impactor. The cut-off of the impactor stage runs at 5.0 μm at a flow rate of 39.0 L/min.
$^c$The maximal achievable FPF is equal to the proportion <5 μm determined in the TOF measuring cell. The powder aerosol that is passed directly over the impactor stage is measured in the TOF measuring cell. The TOF measurement therefore has no connection with particle fractions which have previously been deposited in the measuring device (capsule, HandiHaler, SIP). The FPF on the other hand is based on the weight in the capsule. This includes particle fractions which are deposited before reaching the impactor stage. If the FPF is equal to the particle fraction <5.0 μm found in the TOF measuring cell, then consequently the powder has been completely dispersed and there are no powder deposits in the HandiHaler and SIP.

FIG. 2 shows the monomer content of the antibody after spray drying. It is apparent from this that the less hydrophobic amino acids (glycine, asparagine) have a stabilising effect on the antibody. The hydrophobic amino acids (valine, isoleucine and phenylalanine) by contrast did not have a sufficient stabilising potential for the antibody.

Example 2

Ternary Complexes

Based on Example 1 ternary mixtures were prepared from IgG1, phenylalanine and another excipient. The 3rd component was the very readily water-soluble trisaccharide lactosucrose LS90P.

4 spray solutions were prepared (cf. Table 3). The solvent was purified water. The solid fraction in the spray solution was 3.83% (w/v) in each case.

TABLE 3

Ternary powder compositions of phenylalanine, sugar and protein

| | percentage composition in the powder (phenylalanine/LS90P/protein) | mass ratio of protein/sugar |
|---|---|---|
| powder 1 | 80/10/10 | 1:1 |
| powder 2 | 80/15/5 | 1:3 |
| powder 3 | 60/30/10 | 1:3 |
| powder 4 | 70/25/5 | 1:5 |

The solutions were spray-dried under the following spray conditions:

| | |
|---|---|
| spray dryer: | SD-Micro (Messrs. Niro) |
| entry temperature | 120° C. |
| exit temperature: | 90° C. |
| atomiser gas rate: | 4 kg/h |
| drying gas rate: | 28 kg/h |

FIGS. 3a-3d show the SEM photographs of the different ternary powders. The 4 powders show the same creasing as the powder composition of phenylalanine and IgG1 (cf. Example 1). The 4 ternary powders show no significant differences from one another.

Table 4 shows the aerodynamic properties of the 4 powders. As a result of the addition of lactosucrose the FPF falls only slightly, compared with the binary compositions. The protein stabilisation after spray drying of the ternary powder compositions, on the other hand, is very good. The monomer content for all the formulations was between 98-99% (cf. Table 5)

TABLE 4

Aerodynamic characteristics of the spray-dried powders, measured using the APS*

| Formulation of phenylalanine/LS90P/IgG 1 | MMAD [μm] | FPF [%] |
|---|---|---|
| 80/10/10 | 3.03 | 55.7 |
| 80/15/5 | 2.91 | 64.3 |
| 60/30/10 | 3.35 | 48.4 |
| 70/25/5 | 3.39 | 55.8 |

*The measurements were obtained with the Aerodynamic Particle Sizer.

TABLE 5

Monomer content of the ternary powder compositions

| percentage composition of the powder | | monomer % |
|---|---|---|
| phenylalanine/LS90P/protein | 80/10/10 | 98 |
| phenylalanine/LS90P/protein | 80/15/5 | 98 |
| phenylalanine/LS90P/protein | 60/30/10 | 99 |
| phenylalanine/LS90P/protein | 70/25/5 | 98 |

Example 3

Storage Stability

In the preceding Examples it was demonstrated that phenylalanine on its own and particularly in combination with a sugar gives rise to very good aerodynamic properties of powders after spray drying. Phenylalanine on its own however is unable to stabilise every protein, e.g. the IgG1-antibodies used in Examples 1 and 2. For such proteins, however, stabilisation by the addition of sugar is possible. In this Example the storage stability after spray drying was investigated. On the one hand, the phenylalanine content was varied (80-60% based on the powder). On the other hand, the influence of the proportion of LS90P on the protein stability was examined. Different ratios of protein to sugar were used (cf. Table 5 and 6).

TABLE 5

Composition of spray solution

| | solution 1 | solution 2 | solution 3 |
|---|---|---|---|
| phenylalanine: | 2.29 g/100 mL | 3.06 g/100 mL | 2.29 g/100 mL |
| IgG1: | 1.15 g/100 mL | 338 g/100 mL | 383 mg/100 mL |
| LS90P: | 383 mg/100 mL | 383 mg/100 mL | 1.15 g/100 mL |
| solid fraction: | 3.82% | 3.82% | 3.82% |
| mass ratio of protein/sugar | 3:1 | 1:1 | 1:3 |

The phenylalanine was dissolved with heating (80° C.) in solution. After cooling the solution to ambient temperature the protein and the sugar were added.

TABLE 6

Composition of spray-dried powders

| | powder 1 | powder 2 | powder 3 |
|---|---|---|---|
| phenylalanine: | 60% | 80% | 60% |
| IgG1: | 30% | 10% | 10% |
| LS90P: | 10% | 10% | 30% |
| ratio of protein/sugar | 3:1 | 1:1 | 1:3 |

The solutions were spray-dried under the following spray conditions:

| spray dryer: | SD-Micro (Messrs. Niro) |
|---|---|
| entry temperature | 150° C. |
| exit temperature: | 90° C. |
| atomiser gas rate: | 4 kg/h |
| drying gas rate: | 28 kg/h |

Storage conditions: The powders were stored for 3 months under different storage conditions (25° C./dry, 40° C./dry, 25° C./60% RH) (cf. Table 7 and 8). For the storage condition of 25° C./dry and 40° C./dry the powder was transferred into glass bottles under dry conditions (<30% RH) and sealed with rubber stoppers and a flanged cap.

Storage at 25° C. and 60% relative humidity was created using a saturated saline solution in the desiccator. The desiccator was tempered in the drying cupboard.

TABLE 7

MMAD in μm

| | 2 weeks | | 1 month | | | 2 months | | 3 months | | |
|---|---|---|---|---|---|---|---|---|---|---|
| | starting value | 40° C., dry | 25° C., dry | 25° C., 60% | 40° C., dry | 25° C., dry | 25° C./ 60% | 25° C., dry | 25° C./ 60% | 40° C., dry |
| powder 1 | 4.25 | 4.21 | 4.25 | 4.16 | 4.45 | 4.11 | 4.21 | 4.0 | 4.4 | 4.6 |
| powder 2 | 3.77 | 3.51 | 3.39 | 3.73 | 3.57 | 3.56 | 3.46 | 3.5 | 3.8 | 3.7 |
| powder 3 | 3.73 | 3.75 | 3.80 | 3.68 | 3.81 | 3.75 | 4.03 | 3.8 | 3.9 | 4.0 |

The MMAD shows no significant dependencies between the charges and the storage conditions.

TABLE 8

FPF in percent

|  | starting value | 2 weeks 40° C., dry | 1 month 25° C., dry | 1 month 25° C., 60% | 1 month 40° C., dry | 2 months 25° C., dry | 2 months 25° C./ 60% | 3 months 25° C., dry | 3 months 25° C./ 60% | 3 months 40° C., dry |
|---|---|---|---|---|---|---|---|---|---|---|
| powder 1 | 59.6 | 53.6 | 59.6 | 60.5 | 55.9 | 46.1 | 66.6 | 50.9 | 53.4 | 40.1 |
| powder 2 | 51.2 | 54.0 | 54.8 | 64.5 | 53.6 | 59.2 | 66.7 | 45.2 | 59.3 | 39.0 |
| powder 3 | 45.6 | 49.9 | 47.7 | 58.3 | 55.5 | 40.6 | 55.1 | 40.7 | 55.1 | 36.6 |

The FPF directly after production, i.e. before storage, is 46% (powder 3) to 60% (powder 1). Lowering the phenylalanine content from 80% (powder 2) to 60% (powder 3) has a detrimental effect on the fine particle fraction.

TABLE 9

Monomer contents of the IgG1 antibody in the spray-dried powder

|  | starting value | 2 weeks 40° C., dry | 1 month 25° C., dry | 1 month 25° C., 60% | 1 month 40° C., dry | 2 months 25° C., dry | 2 months 25° C./ 60% | 3 months 25° C., dry | 3 months 25° C./ 60% | 3 months 40° C., dry |
|---|---|---|---|---|---|---|---|---|---|---|
| powder 1 | 97.0 | 96.0 | 97.3 | 90.7 | 97.2 | 97.6 | 90.4 | 97.4 | 88.0 | 95.4 |
| powder 2 | 92.0 | 90.6 | 92.1 | 80.9 | 93.0 | 93.1 | 80.9 | 93.1 | 78.3 | 90.9 |
| powder 3 | 96.3 | 96.1 | 94.9 | 93.1 | 96.3 | 97.2 | 93.0 | 96.1 | 92.0 | 96.1 |

The protein stability after spray drying and storage is shown in Table 9. Table 9 shows the percentage monomer contents of the IgG1 antibody. FIG. 4 shows the relative monomer contents based on the starting values.

The Example shows that the protein can be stored over the tested storage period under dry storage conditions both at 25° C. and also at 40° C. in an almost totally stabilised condition. Under moist conditions there is slight damage to the antibody used in the Example.

The ternary powders thus have a good fine particle fraction and additionally also good storage stability.

Example 4

Storage Stability by Comparison (Dextran- and Phenylalanine-Containing Powders)

The properties of phenylalanine-containing powders were compared with the properties of other, conventional powders (cf. Table 10). With both powders there is only a slight change in the aerodynamic particle size over the storage period (Table 11).

TABLE 10

The spray solutions were spray-dried under the following spray conditions:

|  | phenylalanine/ LS90P/IgG1 (60/10/30) | dextran 1/ isoleucine/IgG1 (65/5/30) |
|---|---|---|
| spray dryer | SDMicro | SDMicro |
| solid fraction | 7.5% | 3.8% |
| entry temperature | 150° C. | 150° C. |

TABLE 10-continued

The spray solutions were spray-dried under the following spray conditions:

|  | phenylalanine/ LS90P/IgG1 (60/10/30) | dextran 1/ isoleucine/IgG1 (65/5/30) |
|---|---|---|
| exit temperature | 85° C. | 90° C. |
| atomiser gas rate | 5 kg/h | 4 kg/h |
| drying gas rate | 28 kg/h | 28 kg/h |

TABLE 11

MMAD [μm]

| storage time | storage conditions | dextran/ isoleucine/IgG1 (65/5/30) | phenylalanine/ LS90P/ IgG1 (60/10/30) |
|---|---|---|---|
| start | — | 3.81 | 4.25 |
| 2 weeks | 40° C., dry | 3.58 | 4.21 |
| 1 month | 25° C., dry | 3.80 | 4.25 |
|  | 25° C./60% | 4.23 | 4.16 |
|  | 40° C., dry | 3.63 | 4.45 |
| 2 months | 25° C., dry | 4.00 | 4.11 |
|  | 25° C./60% | 4.40 | 4.21 |
| 3 months | 25° C., dry | 3.67 | 4.00 |
|  | 25° C./60% | 4.47 | 4.40 |

TABLE 12

Fine particle fractions

| | | dextran/isoleucine/IgG 1 (65/5/30) | | phenylalanine/LS90P/IgG1 (60/10/30) | |
|---|---|---|---|---|---|
| storage time | storage conditions | FPF, % | relative FPF based on the starting value, % | FPF, % | relative FPF based on the starting value, % |
| | start | 33.7 | 100.0 | 59.6 | 100.0 |
| 2 weeks | 40° C., dry | 21.1 | 62.7 | 53.6 | 89.9 |
| 1 month | 25° C. dry | 26.2 | 77.9 | 59.6 | 100.0 |
| | 25° C./60% | 16.4 | 48.8 | 60.5 | 101.5 |
| | 40° C., dry | 22.4 | 66.5 | 55.9 | 93.8 |
| 2 months | 25° C., dry | 24.0 | 71.1 | 46.1 | 77.3 |
| | 25° C./60% | 14.6 | 43.4 | 66.6 | 111.7 |
| 3 months | 25° C., dry | 23.3 | 69.1 | 50.9 | 85.4 |
| | 25° C./60% | 15.2 | 45.1 | 53.4 | 89.6 |

The phenylalanine-containing powder has a substantially better FPF compared with a dextran-containing powder (59.6% as against 33.7%, see Table 12/FIG. 5). As the aerodynamic particle sizes of the two powders are only slightly different or the phenylalanine-containing powder even has a slightly higher MMAD (cf. Table 11), the differences in the FPF can be put down to the dispersion characteristics of the powders as they are expelled from the capsule. This means that the phenylalanine-containing powder can be dispersed substantially better and hence interparticulate interactions are reduced, compared with the corresponding dextran-containing powder.

FIG. 6 shows the relative FPF based on the starting value of the stability. It is apparent here that the phenylalanine-containing powder has substantially smaller collapses in the FPF over the storage period. Phenylalanine is particularly advantageous at higher humidities. Whereas in dextran-containing powder the FPF falls to 45-49% of the initial value, the phenylalanine-containing powder even shows an increase in the FPF after 2 months' storage and after 3 months only a slight drop to 89% of the starting value.

This result particularly underlines the suitability of the ternary powder compositions at elevated humidities. The conventional spray-dried powders generally show a major collapse in their aerodynamic characteristics. Phenylalanine, on the other hand, results in a stabilisation of the aerodynamics or, as shown in this Example, even an improvement in them.

Morphology of the Powders:

As illustrated in FIG. 7 and FIG. 8, neither powder (phenylalanine-containing powder in FIG. 7, dextran-containing powder in FIG. 8) contains any large agglomerations of powder. Moreover multiple indentations can be seen in both formulations. An essential difference between the two morphologies is the higher surface roughness of the phenylalanine-containing powder. This increased surface roughness is presumably also the reason for the better dispersion characteristics.

The addition of the hydrophobic amino acids (isoleucine or phenylalanine) should cause the surfaces of the particles to be at least partly hydrophobic in both powders. Here again it is demonstrated that simply making the surface hydrophobic is far less efficient for its aerodynamic properties than inducing rough surface structures, as is the case with phenylalanine.

Example 5

Spray Drying at Different pH-Values

In this Example a spray solution of a defined composition (cf. Table 13) was adjusted to different pH values and sprayed.

The spray conditions are shown in Table 14.

TABLE 13

| Composition of the spray solutions | | | |
|---|---|---|---|
| | spray solution 1 | spray solution 2 | spray solution 3 |
| phenylalanine: | 2.29 g/100 mL | 2.29 g/100 mL | 2.29 g/100 mL |
| IgG1: | 1.15 g/100 mL | 1.15 g/100 mL | 1.15 g/100 mL |
| LS90P: | 383 mg/100 mL | 383 mg/100 mL | 383 mg/100 mL |
| buffer | 1.6 mM glycine/ 25 mM histidine, pH 5.9 | 25 mM TRIS, pH 7.4 | 25 mM TRIS pH 9.0 |
| solid fraction | 4.2% (w/w) | 4.1% (w/w) | 4.1% (w/w) |

TABLE 14

| Spray conditions | |
|---|---|
| spray dryer | Büchi B191 |
| entry temperature | 150° C. |
| exit temperature | 90° C. |
| atomiser gas rate | 700 L/h |
| drying gas rate | 100% aspirator power |

TABLE 15

| Results | | | |
|---|---|---|---|
| | powder 1 | powder 2 | powder 3 |
| MMAD, μm | 3.9 | 4.4 | 5.2 |
| FPF, % | 44.7 | 51.8 | 48.9 |
| expelled mass, % | 91.7 | 87.0 | 89.2 |
| crystallinity | partly crystalline | partly crystalline | partly crystalline |
| monomer content, % | 98 | 97 | 90 |

The aerodynamic characteristics (FPF, expelled mass) of the powders shown in Table 15 show no essential differences. The prepared powders were partly crystalline in each case. Accordingly the pH value of the spray solution is not decisive for the powder qualities (dispersibility/inhalability) and the spray quality of the phenylalanine.

The protein stabilisation depends on the pH value of the spray solution. The antibody used is more stable at low pH values. However, protein stabilisation particularly compared with binary compositions (cf. FIG. 2) can also be achieved at high pH values of 9.0.

Example 6

Spray Drying with Different Amounts of Phenylalanine

In this Example the phenylalanine content in the spray-dried powder is reduced from 50% w/w to 20% w/w. The compositions in the powder are compiled in Table 16. The spray conditions are shown in Table 17.

TABLE 16

Composition of the spray-dried powders

|  | powder 1 | powder 2 | powder 3 | powder 4 |
|---|---|---|---|---|
| phenylalanine | 50% w/w | 40% w/w | 30% w/w | 20% w/w |
| IgG1 | 30% w/w | 30% w/w | 30% w/w | 30% w/w |
| LS90P | 20% w/w | 30% w/w | 40% w/w | 50% w/w |

TABLE 17

Spraying conditions

| spray dryer | Büchi B191 |
|---|---|
| solid fraction | 3.82% |
| entry temperature | 150° C. |
| exit temperature | 90° C. |
| atomiser gas rate | 700 L/h |
| drying gas rate | 100% aspirator power |

Figure 9:
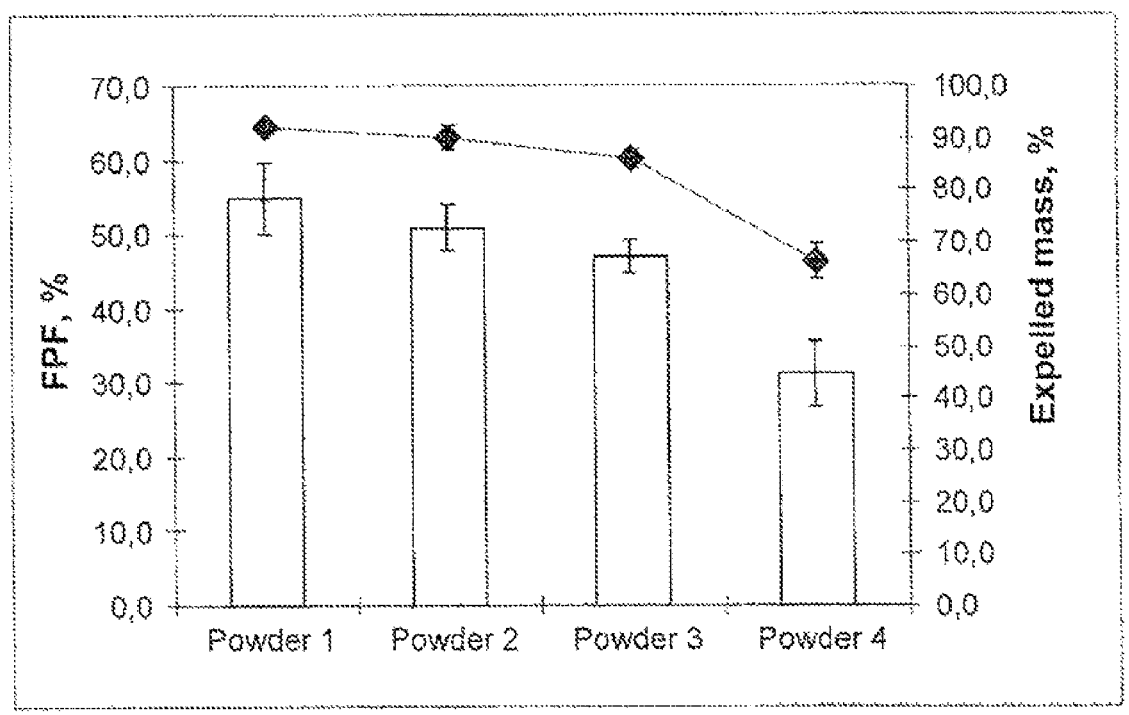

FIG. 9 shows the aerodynamic characteristics of the spray-dried powders as a function of the phenylalanine content in the powder. According to this Figure the phenylalanine content in the spray-dried powder may be reduced to 30% (w/w). If the phenylalanine content is further lowered to 20% (w/w) both the fine particle fraction and the expelled mass are reduced substantially.

Figure 10A:
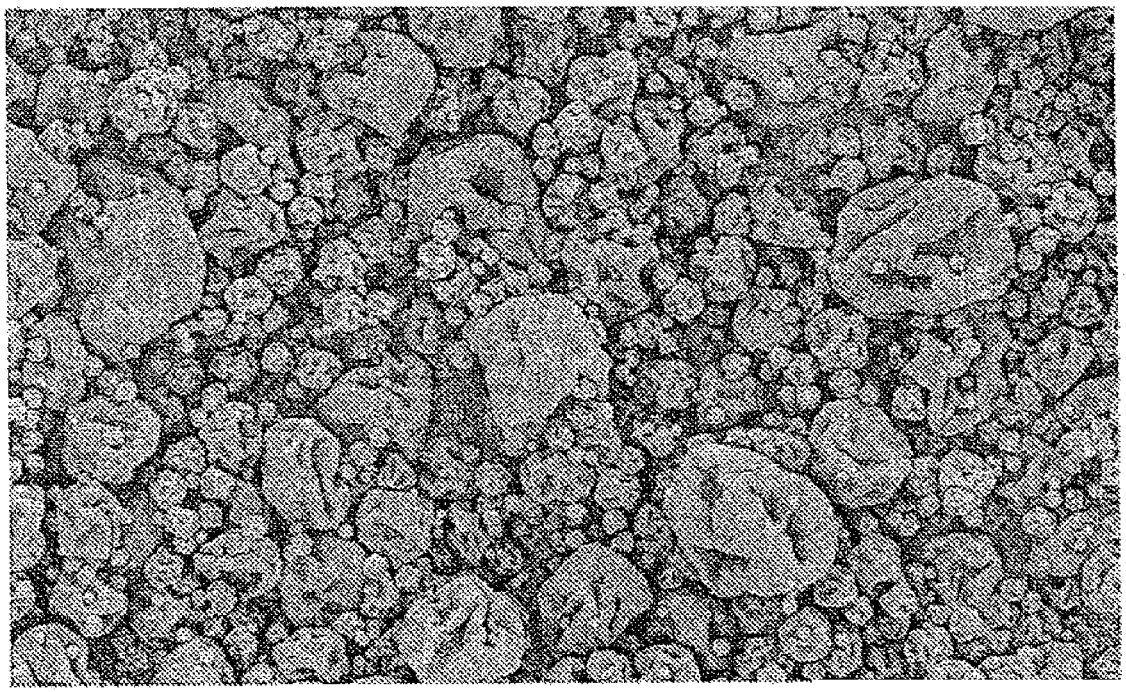
Figure 10B:
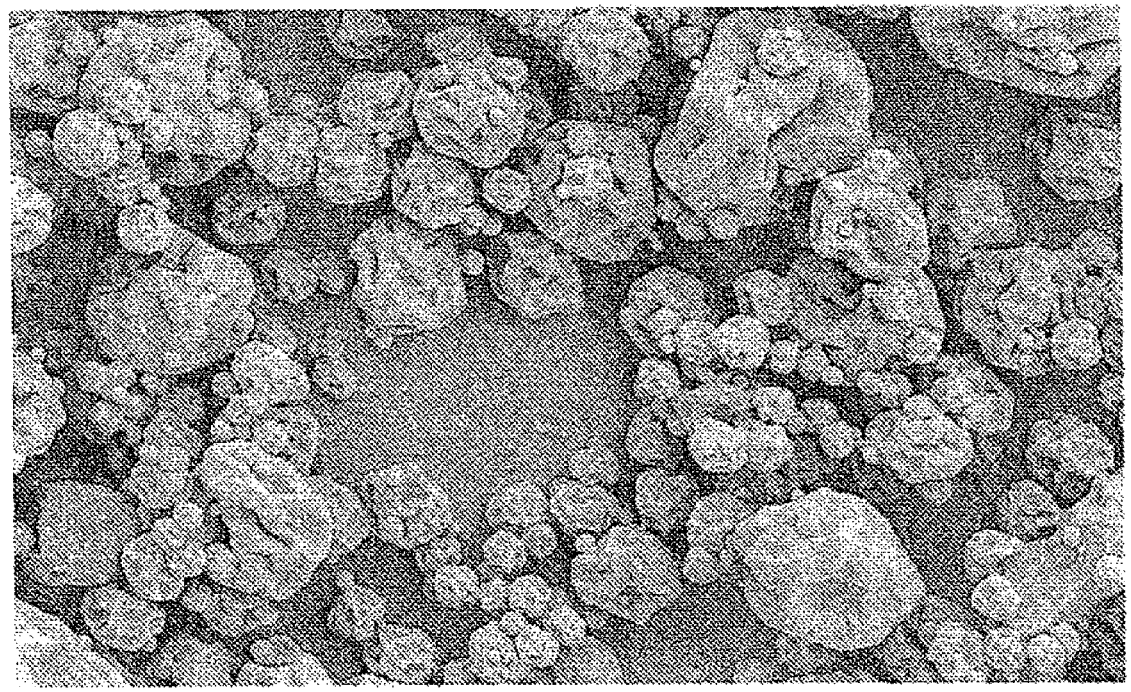
Figure 10C:
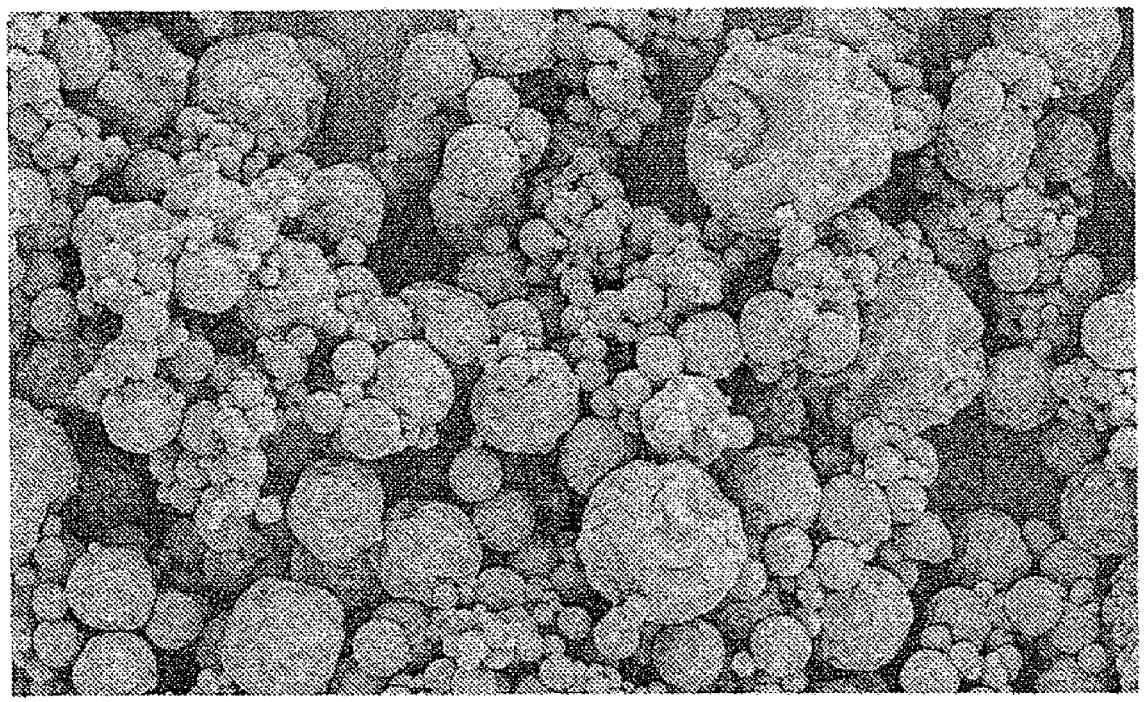
Figure 10:
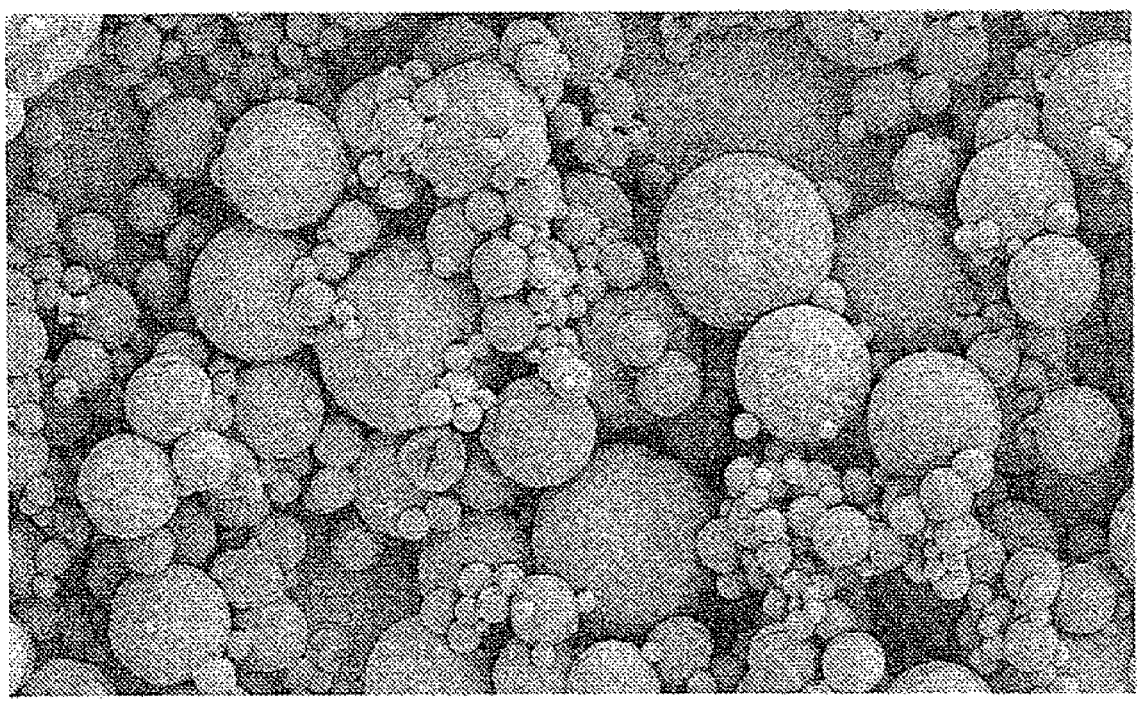

The particle morphology is highly dependent on the phenylalanine content in the spray-dried powder. At phenylalanine contents of 50% (w/w), 40% (w/w) and 30% (w/w) highly creased, raisin-like particles are obtained (FIG. 10a-10c). When the phenylalanine content is reduced to 20% the intensity of folding decreases sharply. The change in the particle morphology correlates with the deterioration in the aerodynamic characteristics of the powder. This means that the positive effect of the phenylalanine when spray-drying spray solutions only becomes apparent upwards of 30% (w/w).

Example 7

Spray Drying Various Proteins

In this Example the hormone calcitonin and the enzyme lysozyme were spray-dried, in addition to an IgG type antibody. The compositions of the powders prepared are shown in Table 18 and the spray conditions are specified in Table 19.

TABLE 18

Composition of the spray-dried powders

| powder 1 | powder 2 | powder 3 |
|---|---|---|
| 60% w/w phenylalanine | 60% w/w phenylalanine | 60% w/w phenylalanine |
| 10% w/w IgG | 10% w/w lysozyme | 10% w/w calcitonin |
| 30% w/w LS90P | 30% w/w LS90P | 30% w/w LS90P |

TABLE 19

Spray conditions

| spray dryer | Büchi B191 |
|---|---|
| solid fraction | 3.8% w/v |
| entry temperature | 150° C. |
| exit temperature | 90° C. |

TABLE 19-continued

Spray conditions

| atomiser gas rate | 700 L/h |
|---|---|
| drying gas rate | 100% aspirator power |

Figure 11:
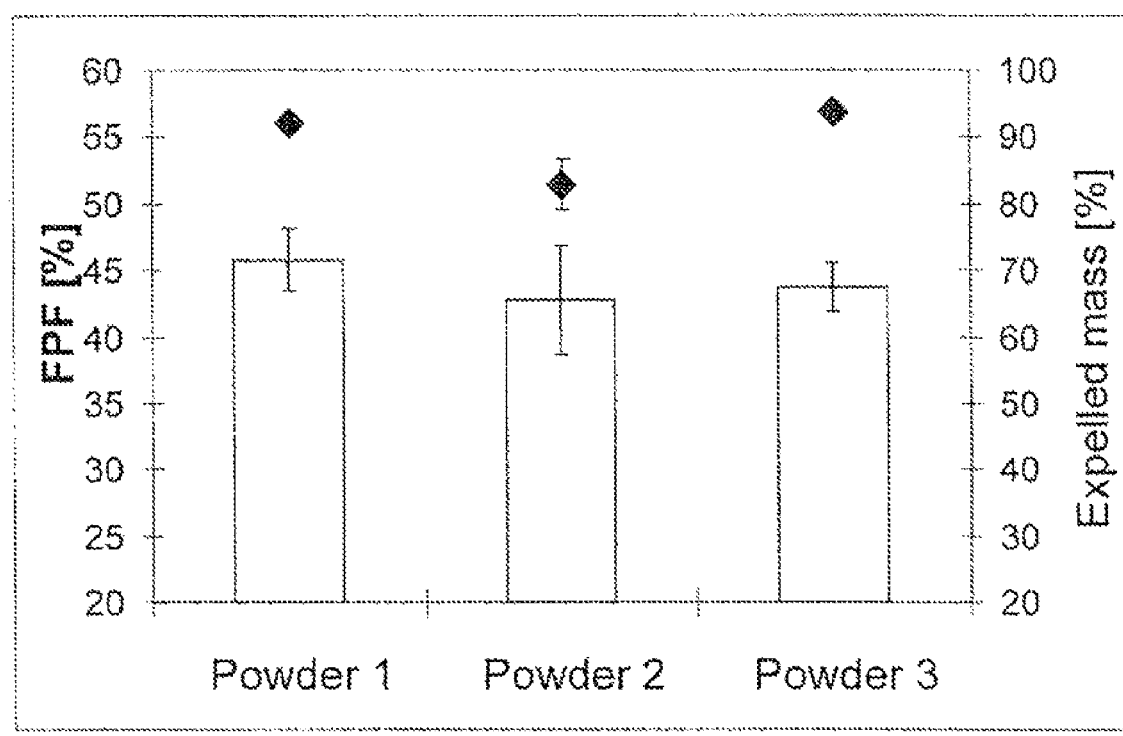

FIG. 11 shows the fine particle fraction and the expelled mass of the spray-dried powders 1-3. The nature of the protein is thus not critical to the aerodynamic characteristics of the spray-dried powders.

Example 8

Preparation of Spray-Dried Powders with Different Further Excipients

In this series of experiments, instead of LS90P other excipients were spray-dried with phenylalanine and an IgG1 antibody. The compositions of the prepared powders are shown in Table 20, the spray conditions in Table 21.

TABLE 20

Composition of the spray-dried powders

| powder 1 | powder 2 | powder 3 | powder 4 |
|---|---|---|---|
| 60% w/w phenylalanine | 60% w/w phenylalanine | 60% w/w phenylalanine | 60% w/w phenylalanine |
| 30% w/w IgG | 30% w/w IgG | 30% w/w IgG | 30% w/w IgG |
| 10% w/w saccharose | 10% w/w mannitol | 10% w/w glycine | 10% w/w polyvinyl-pyrrolidone (PVP) |

TABLE 21

Spray conditions

| spray dryer | Büchi B191 |
|---|---|
| solid fraction | 3.8% |
| entry temperature | 150° C. |
| exit temperature | 90° C. |
| atomiser gas rate | 700 L/h |
| drying gas rate | 100% aspirator power |

Figure 12:
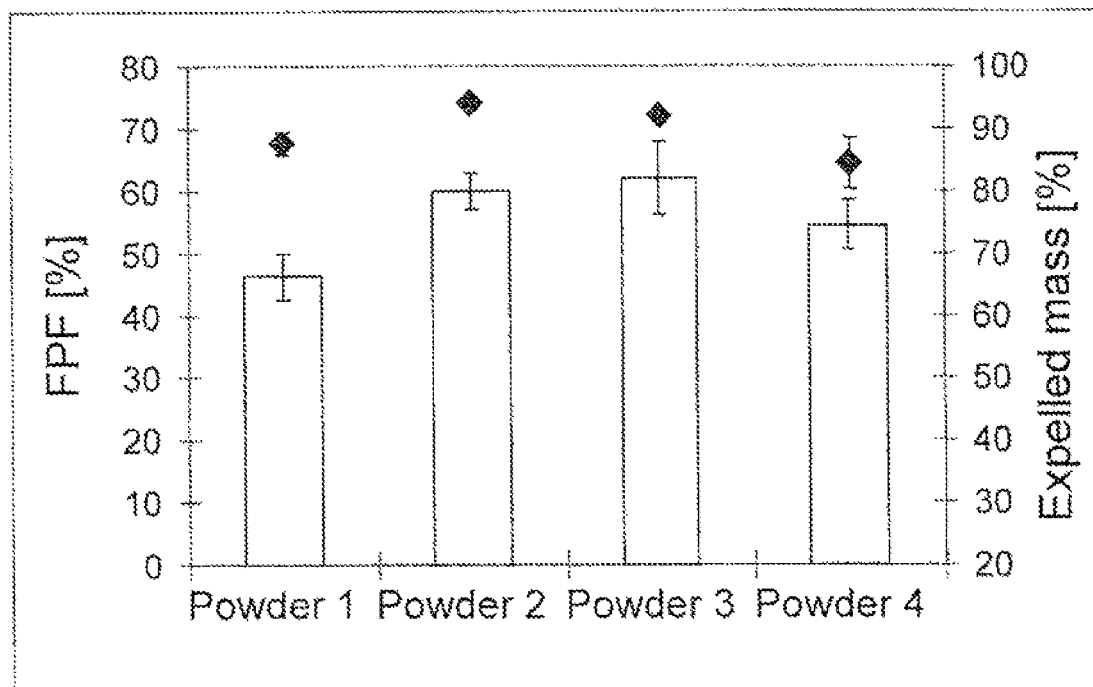

FIG. 12 shows the fine particle fractions and the expelled masses. The fine particle fractions are very high with the excipients tested (saccharose: 46%, mannitol: 60%, glycine: 62%, PVP: 63%). It has also been shown that by a skilful choice of excipients the positive effect of phenylalanine on the spray drying process can be further improved. The further excipient is not restricted to one category of substances. It may be, as in this example, a sugar or sugar alcohol, an amino acid or a polymer. What is crucial to the use of the further excipient is the stabilisation of the protein during spray drying. Table 22 shows the monomer contents of the antibody used. It is apparent that by adding another excipient the protein can be stabilised, compared with binary mixtures of phenylalanine and IgG1 (cf. FIG. 2).

TABLE 22

|  | powder 1 | powder 2 | powder 3 | powder 4 |
|---|---|---|---|---|
| monomer content IgG1 | 98% | 98% | 95% | 94% |

Example 9

Spray Drying Using Crystallisation Inhibitors

This Example is intended to demonstrate that the spray-dried powders can be optimised by using crystallisation inhibitors. For this purpose different powders were prepared as shown in Table 23.

TABLE 23

Compositions of the powders

| | composition | method of preparation |
|---|---|---|
| powder 1 | 60% phenylalanine 40% LS90P | spray drying (SDMicro) |
| powder 2 | 60% phenylalanine 30% LS90P 10% IgG1 | spray drying (SDMicro) |
| powder 3 | 60% phenylalanine 30% LS90P 10% lysozyme | spray drying (Büchi B191) |
| powder 4 | 60% phenylalanine 30% LS90P 10% calcitonin | spray drying (Büchi B191) |
| powder 5 | 100% LS90P | freeze-drying (GT-12B) |

The spray conditions in the Buchi B191 and SDMicro are compiled in Table 24.

TABLE 24

Spray conditions

| | | |
|---|---|---|
| spray dryer | Büchi B191 | SDMicro |
| solid fraction | 3.8% | 3.8% |
| entry temperature | 150° C. | 150° C. |
| exit temperature | 90° C. | 90° C. |
| atomiser gas rate | 700 L/h | 4 kg/h |
| drying gas rate | 100% aspirator power | 28 kg/h |

The aim of freeze-drying an aqueous LS90P solution was to prepare X-ray-amorphous powder. For this, an aqueous solution with a small solid fraction (5 g/100 mL) was prepared and freeze-dried as described in Table 25.

TABLE 25

Temperature and pressure programme of the freeze-drying

| Process step | time [hh:mm] | temperature [° C.] | pressure [mbar] |
|---|---|---|---|
| start | — | 20 | — |
| freezing (temperature gradient) | 01:30 | −50 | — |
| freezing (holding step) | 06:30 | −50 | — |
| after-drying (pressure gradient) | 00:01 | −50 | 0.016 |
| main drying (temperature gradient) | 07:00 | −40 | 0.016 |
| main drying (holding step) | 23:00 | −40 | 0.016 |
| main drying (temperature gradient) | 03:20 | −23 | 0.016 |
| main drying (holding step) | 30:00 | −23 | 0.016 |
| main drying (temperature gradient) | 02:00 | 20 | 0.016 |
| after-drying (pressure gradient) | 00:01 | 20 | 0.001 |
| after-drying (holding step) | 17:00 | 20 | 0.001 |

Figure 13:
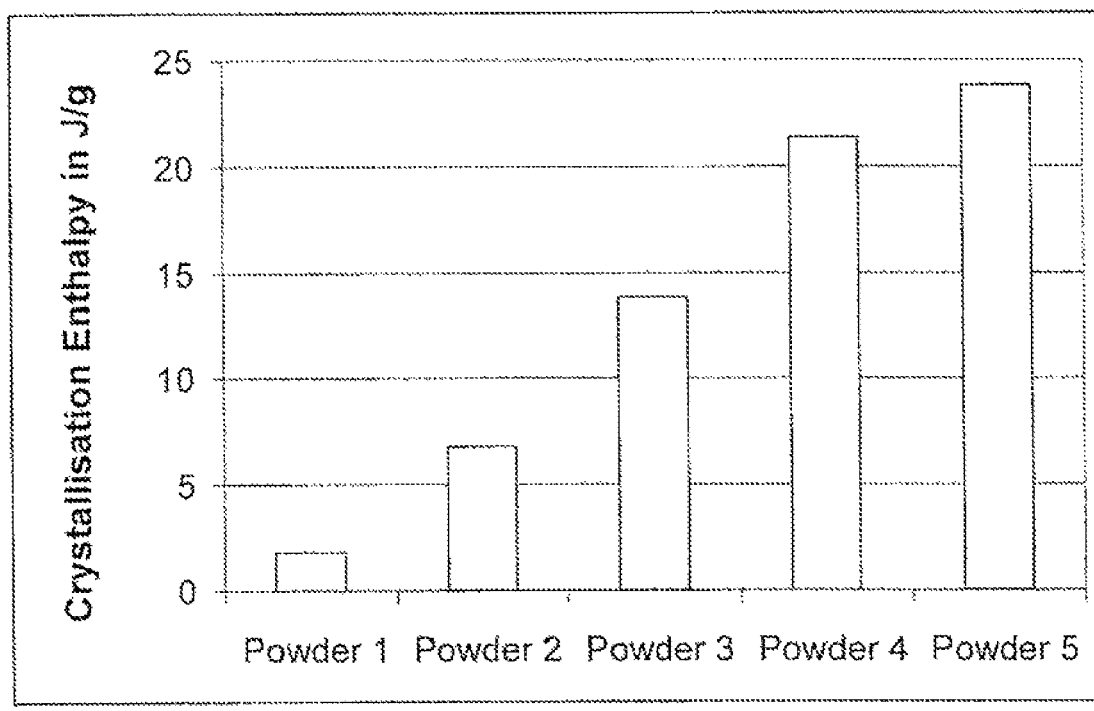

FIG. 13 shows the recrystallisation enthalpies of LS90P after heating the powders in a DSC apparatus (DSC821/Mettler Toledo). It is found that the crystallisation enthalpy based on the proportion by mass of the protein used depends to a great extent on the protein. Thus, the crystallisation enthalpy increases in the order IgG1 (6.8 J/g), lysozyme (13.9 J/g), calcitonin (21.3 J/g) and thus also the amorphous fraction of the LS90P after spray drying. As the LS90P in the powder formulations in question is the protein-stabilising component in the powder, it is desirable to have a high amorphous fraction of LS90P in the powder. In a further series of experiments, HSA was therefore added to the spray solution as a crystallisation inhibitor. The spray drying was carried out analogously to Table 26. The composition of the powder was: 60% phenylalanine/30% LS90P/1% HSA/9% IgG1.

The crystallisation enthalpy of LS90P was 24.3 J/g and corresponds to the X-ray-amorphous LS90P (23.8 J/g). Based on the IgG1-containing powder 2 the powder characteristics based on the amorphous nature of the powder can be optimised by the addition of small amounts of HSA.

TABLE 26

Spray conditions

| | |
|---|---|
| spray dryer | SDMicro |
| solid fraction | 3.8% |
| entry temperature | 150° C. |
| exit temperature | 100° C. |
| atomiser gas rate | 4 kg/h |
| drying gas rate | 28 kg/h |

Example 10

Comparison of Various Aromatic Amino Acids

This Example sets out to compare the aromatic amino acids tryptophan and histidine with comparable phenylalanine-containing powders. The aromatic amino acid tyrosine is ruled out as a potential excipient for spray drying, as this amino acid is not sufficiently water-soluble. Tryptophan is also very poorly soluble in water, compared with phenylalanine, so that tryptophan contents of not more than 20% w/w can be used to prepare pharmaceutically useful powders. In order to compare the spraying characteristics of the aromatic amino acids, in each case powders containing 20% amino acid were prepared. Table 27 shows the compositions of the powders and Table 28 shows the spray conditions.

TABLE 27

Composition of the spray-dried powders

| powder 1 | powder 2 | powder 3 |
|---|---|---|
| 20% w/w tryptophan | 20% w/w histidine | 20% w/w phenylalanine |
| 30% w/w IgG 1 | 30% w/w IgG 1 | 30% w/w IgG 1 |
| 50% w/w LS90P | 50% w/w LS90P | 50% w/w LS90P |

TABLE 28

Spray conditions

| | |
|---|---|
| spray dryer | Büchi B191 |
| solid fraction | 3.8% |
| entry temperature | 150° C. |
| exit temperature | 90° C. |

TABLE 28-continued

Spray conditions

| | |
|---|---|
| atomiser gas rate | 700 L/h |
| drying gas rate | 100% aspirator power |

Figure 14:
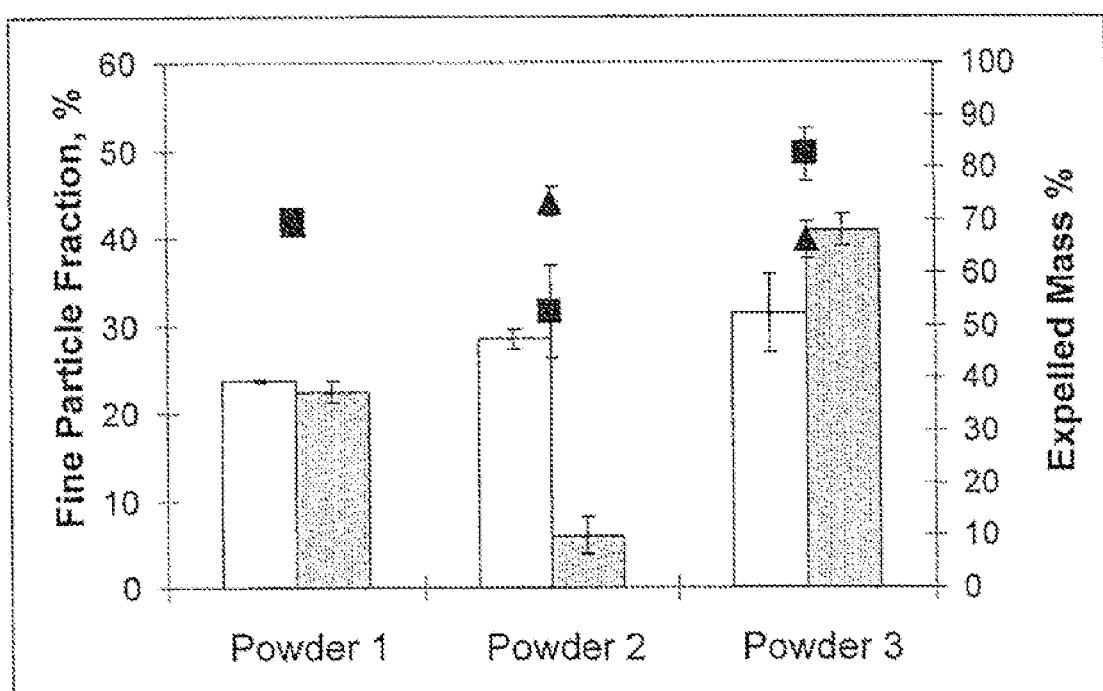

The fine particle fractions were slightly better after spray drying with the phenylalanine-containing powder (cf. FIG. 14).

A major advantage of the phenylalanine-containing powder over the histidine-containing powder is its lower moisture-sensitivity. Whereas the FPF of the histidine-containing powder breaks down after exposure to 50% relative humidity, in the case of the phenylalanine-containing powder the FPF is even improved after exposure to moisture. Corresponding characteristics can also be observed in relation to the expelled mass. In the case of the histidine-containing powder the expelled mass decreases on exposure to moisture, whereas in the case of the phenylalanine-containing powder it increases.

The tryptophan-containing powder shows no change in the FPF and expelled mass as a result of humidity. A disadvantage of this amino acid compared with phenylalanine is its very low water-solubility, as already mentioned hereinbefore.

Histidine was further compared with corresponding phenylalanine-containing powders (cf. Table 29). The preparation method was analogous to the spraying conditions specified in Table 28.

TABLE 29

| powder 4 | powder 5 | powder 6 | powder 7 |
|---|---|---|---|
| 30% w/w histidine | 60% w/w histidine | 30% w/w phenylalanine | 60% w/w phenylalanine |
| 30% w/w IgG 1 | 30% w/w IgG 1 | 30% w/w IgG 1 | 30% w/w IgG 1 |
| 50% w/w LS90P | 10% w/w LS90P | 50% w/w LS90P | 10% w/w LS90P |

Whereas the powders 4 and 6 have similar aerodynamic properties, the phenylalanine-containing powder 7 exhibits a substantially better fine particle fraction compared with the corresponding histidine-containing powder 5 (cf. Table 30).

What is particularly noticeable is the difference in the aerodynamics after exposure to humidity (cf. Table 31). As a result of the influence of moisture the FPF breaks down almost totally in the histidine-containing powders tested. Phenylalanine-containing powders on the other hand show a slight improvement in their aerodynamic characteristics.

TABLE 30

FPF and expelled mass of spray-dried powders without moisture-proof packaging

| powder | FPF, % | expelled mass, μm |
|---|---|---|
| powder 4 | 40.5 | 88.5 |
| powder 5 | 28.1 | 84.4 |
| powder 6 | 47.0 | 85.9 |
| powder 7 | 49.7 | 92.1 |

TABLE 31

FPF and expelled mass of spray-dried powders with moisture-proof packaging (50% humidity/20 hours/ambient temperature)

| powder | FPF, % | expelled mass, μm |
|---|---|---|
| powder 4 | 3.3 | 66.6 |
| powder 5 | 5.4 | 70.5 |
| powder 6 | 57.2 | 85.9 |
| powder 7 | 54.9 | 88.6 |

To summarise, it can be stated that the positive properties of phenylalanine on spray drying cannot be achieved using other aromatic amino acids.

The invention claimed is:

1. A spray-dried powder comprising a protein and phenylalanine, wherein said powder comprises at least 60% (w/w) phenylalanine and at least one excipient comprising a sugar or a polyol.

2. The powder according to claim 1, wherein said powder comprises at least 65% (w/w) phenylalanine.

3. The powder according to claim 1, wherein said powder comprises at least 65% (w/w), at least 70% (w/w), at least 75% (w/w), at least 80% (w/w), at least 85% (w/w), at least 90% (w/w), at least 95% (w/w), at least 99% (w/w) or at least 99.99% (w/w) phenylalanine.

4. The powder according to claim 1, wherein the proportion of phenylalanine in said powder is 60% (w/w) to 99.99% (w/w), 65% (w/w) to 99.99% (w/w), 60% (w/w) to 70% (w/w), 60% (w/w) to 90% (w/w), or 60% (w/w) to 80% (w/w).

5. The powder according to claim 1, wherein said sugar is a non-reducing sugar selected from the group consisting of a disaccharide and an oligosaccharide.

6. The powder according to claim 5, wherein said disaccharide is saccharose or trehalose.

7. The powder according to claim 5, wherein said oligosaccharide is a trisaccharide.

8. The powder according to claim 5, wherein said trisaccharide is lactosucrose.

9. The powder according to claim 1, wherein said polyol is mannitol.

10. The powder according to claim 5, wherein the proportion of said sugar in said powder is at most 35% (w/w).

11. The powder according to claim 10, wherein the proportion of said sugar in said powder is 5% (w/w), 10% (w/w), 15% (w/w), 20% (w/w), 25% (w/w), 30% (w/w) or 35% (w/w).

12. The powder according to claim 10, wherein the proportion of said sugar in said powder is 10 to 20% (w/w).

13. The powder according to claim 1, wherein the mass ratio of sugar to protein in said powder is between 1:10 to 10:1.

14. The powder according to claim 13, wherein said ratio is 1:3 to 5:1.

15. The powder according to claim 1, wherein said protein is an active substance.

16. The powder according to claim 15, wherein said active substance is a pharmaceutical active substance.

17. The powder according to claim 16, wherein said pharmaceutical active substance is an antibody, an antibody fragment, a fusion protein with parts of antibodies or a conjugated antibody, a growth factor, a hormone or an enzyme.

18. The powder according to claim 1, wherein the protein content is 0.01 to less than 40% (w/w), 1 to less than 40% (w/w), 10 to less than 40% (w/w) or 30 to less than 40% (w/w).

19. The powder according to claim 1, wherein the ratio by mass of phenylalanine/sugar/protein is 99.89/0.1/0.01, 90/9/1, 90/1/9, 80/10/10, or 60/10/30.

20. The powder according to claim 1, wherein said powder consists of phenylalanine/lactosucrose or saccharose/and a small protein in a mass ratio of 60/10/30.

21. The powder according to claim 20, wherein said small protein is a growth factor, insulin, interferon or calcitonin.

22. The powder according to claim 1, wherein the mean aerodynamic particle diameter of the powder particles is less than 10 μm, less than 7.5 μm, or in the range between 1-6 μm or 3-6 μm or 5-7 μm.

23. A pharmaceutical composition comprising a powder according to claim 1.

24. A spray-dried powder comprising a protein and phenylalanine wherein said powder comprises at least 40% (w/w) phenylalanine and at least one excipient comprising a sugar or a polyol.

25. The powder according to claim 24, wherein the mean aerodynamic particle diameter of the powder particles is less than 10 μm.

26. A method of preparing a powder according to claim 1, comprising the steps of:
  a) preparing a phenylalanine solution,
  b) adding at least one protein,
  c) spraying the solution or suspension obtained in step b) at an inflow temperature of 90-200° C. and an outflow temperature of 40-150° C., and
  d) separating the particles formed in step c) from the drying gas.

27. The method according to claim 26, wherein at least one further excipient is added to said phenylalanine solution.

28. The method according to claim 26, wherein said protein is a pharmaceutical active substance.

29. The method according to claim 26, wherein the following additional steps are carried out between steps a) and b):
  i) heating the phenylalanine solution, and,
  ii) cooling the phenylalanine solution to below the denaturing temperature of the particular protein to be added in each case.

30. The method according to claim 29, wherein said phenylalanine solution is heated to 80° C.

31. The method according to claim 29, wherein said phenylalanine solution is cooled to ambient temperature.

32. The method according to claim 26, wherein said solution or suspension is sprayed in step c) by means of at least one pressure nozzle or at least one rotary evaporator or at least one venturi nozzle or at least one ultrasound nebuliser or at least one two-substance nozzle.

33. The method according to claim 26, wherein the separation of the particles in step d) is carried out in at least one particle separator device operable to separate particles.

34. The method according to claim 33, wherein the separation of the particles in step d) is carried out in at least one cyclone device operable to separate particles.

35. A method of treating a disease or a condition, said method comprising the step of administering to a patient in need thereof a therapeutically effective amount of a powder according to claim 1 or a pharmaceutical composition comprising a powder according to claim 1, wherein the powder comprises a pharmaceutically active protein.

36. The method according to claim 35, wherein said powder or said pharmaceutical composition is administered to said patient as an inhaled medicament.

37. The method according to claim 35, wherein said disease or condition is a respiratory complaint or a systemic disease.

38. The method according to claim 35, wherein said disease is selected from the group consisting of lung cancer, inflammation of the lung, cystic fibrosis, chronic obstructive pulmonary disease (COPD), asthma, inflammatory diseases or conditions, and viral diseases or conditions.

39. The method according to claim 38, wherein said viral disease is caused by respiratory-syncytial virus (RSV).

\* \* \* \* \*